US007265155B2

(12) United States Patent
Artman et al.

(10) Patent No.: US 7,265,155 B2
(45) Date of Patent: *Sep. 4, 2007

(54) TREATING A VARIETY OF PATHOLOGICAL CONDITIONS, INCLUDING SPASTICITY AND CONVULSIONS, BY EFFECTING A MODULATION OF CNS ACTIVITY WITH ISOVALERAMIDE, ISOVALERIC ACID, OR A RELATED COMPOUND

(75) Inventors: Linda D. Artman, Salt Lake City, UT (US); Manuel Balandrin, Sandy, UT (US); Robert L. Smith, Lansdale, PA (US)

(73) Assignee: NBS Pharmaceuticals, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/614,344

(22) Filed: Jul. 8, 2003

(65) Prior Publication Data

US 2004/0072900 A1    Apr. 15, 2004

Related U.S. Application Data

(60) Division of application No. 09/258,882, filed on Mar. 1, 1999, now Pat. No. 6,589,994, which is a continuation-in-part of application No. PCT/US97/15272, filed on Aug. 29, 1997.

(60) Provisional application No. 60/025,050, filed on Aug. 30, 1996.

(51) Int. Cl.
*A61K 31/155*    (2006.01)
(52) U.S. Cl. .................................. 514/629; 514/923
(58) Field of Classification Search ................ 514/629, 514/923
See application file for complete search history.

(56) References Cited

U.S. PATENT DOCUMENTS

| | | | | |
|---|---|---|---|---|
| 3,485,851 | A | 12/1969 | Thies | 260/345.2 |
| 4,933,324 | A | 6/1990 | Shashoua | 514/17 |
| 4,939,174 | A | 7/1990 | Shashoua | 514/549 |
| 5,506,268 | A * | 4/1996 | Balandrin et al. | 514/629 |
| 5,763,494 | A | 6/1998 | Balandrin et al. | 514/629 |
| 5,994,392 | A | 11/1999 | Shashoua | 514/78 |
| 6,107,499 | A | 8/2000 | Shashoua | 554/78 |
| 6,258,836 | B1 | 7/2001 | Shashoua | 526/437 |
| 6,589,994 | B1 * | 7/2003 | Artman et al. | 514/629 |

FOREIGN PATENT DOCUMENTS

| | | |
|---|---|---|
| WO | 94/28888 | 12/1994 |
| WO | 94 28888 A | 12/1994 |
| WO | WO94/28888 | 12/1994 |
| WO | 97/34596 | 9/1997 |
| WO | WO97/34596 | 9/1997 |
| WO | 98/08498 | 3/1998 |
| WO | 98 08498 A | 3/1998 |
| WO | WO98/08498 | 3/1998 |
| WO | WO99/44623 | 3/1999 |
| WO | WO 01/28516 | 10/2000 |

OTHER PUBLICATIONS

Schon and Blau, J Neurol Neurosurg Psychiatry, Sep. 1987: 50(9):1148-1152.*
Dorland's Medical Dictionary 27th ed. p. 379.*
Pharmacotherapy, A Pathophysiologic Approach, Dipiro et al.2nd ed. 1991, pp. 1232, 1238).*
Drug facts and comparisons 1999 ed. pp. 1595-1597("Drug Facts").*
Pharmacotherapy, A Pathophysiologic Approach, Dipiro et al. 2nd ed. 1991, pp. 1232 & 1238.*
Drug Facts and Comparisons. 1999 ed. pp. 1595-1597 ("Drug Facts").*
Julius A. Vida "Advances in Anticonvulsant Drug Development"; Anticonvulsants (1997) pp. 1-9; Academic Press.
Julius A. Vida "Noncyclic Anticonvulsants"; Anticonvulsants (1977) pp. 577-619; Academic Press.
Salim Hadad, et al. "Pharmacokinetic Analysis and Antiepileptic Activity of N-Valproyl Deratives of GABA and Glycine"; Pharmaceutical Research (1995), pp. 905-907; Plenum Publishing Corporation.
Abdulla Haj-Yehia, et al. "Structure-Pharmacokinetic Relationships in a Series of Short Fatty Acid Amides that Possess Anticonvulsant Activity"; Journal Of Pharmaceutical Sciences; (Aug. 1990); pp. 719-724; vol. 79, No. 8.
Abdulla Haj-Yehia, et al. "Pharmacokinetic Analysis of the Structural Requirements for Forming "Stable" Analogues of Valpromide"; Pharmaceutical Research; (1992) pp. 1058-1063; vol. 9, No. 8; Plenum Publishing Corporation.
Georges Taillandier, et al. "Recherches dans la série dipropylacétique XII. Acides et alcools aliphatiques ramifiés anticonvulsivants"; Eur. J. Med. Chem—Chemical Therapeutica; (Sep.-Oct. 1975-10); N° 5; pp. 453-462.
Joel G. Hardman, Ph.D., et al. "The Pharmacological Basis of Therapeutics" 10th Edition; (2001).
H. Steve White, et al. "Experimental Selection, Quantification, and Evaluation of Antiepileptic Drugs" Antiepileptic Drugs, Fourth Edition; (1995); pp. 99-110; Raven Press, New York.
Walter Sneader "Drug Discovers: The Evolution of Modern Medicines" (1985), pp. 24-47; John Wil y & Sons.
Julius A. Vida "Anticonvulsants"; Principles Of Modern Chemistry, 4th Edition; (1995); pp. 182-198; Williams and Wilkins.

(Continued)

Primary Examiner—Sreeni Padmanabhan
Assistant Examiner—Renee Claytor
(74) Attorney, Agent, or Firm—TraskBritt

(57) ABSTRACT

Preparations and extracts of valerian, as well as isovaleramide, isovaleric acid, and certain structurally related compounds, exhibit clinically significant pharmacological properties that implicate a treatment for a variety of pathological conditions, including spasticity and convulsions, which are ameliorated by effecting a modulation of CNS activity. The compositions in question generally are non-cytotoxic and do not elicit weakness or sedative activity at doses that are effective for the symptomatic treatment of such pathological conditions.

2 Claims, 7 Drawing Sheets

OTHER PUBLICATIONS

David A. Williams, et al. (Table of Contents) "Foye's Principles of Medicinal Chemistry" 5th Edition (2002).

W. Löscher, et al. "Strategies in antiepileptic drug development: is rational drug design superior to random screening and structural variation?" Epilepsy Research; (1994) pp. 95-134.

A. Haj-Yehia, et al. "Structure-pharmacokinetic relationships in a series of valpromide derivatives with antiepileptic activity" PMID: 2510141 [PubMed—indexed for MEDLINE].

A. Haj-Yehia, et al. "Structure-pharmacokinetic relationships in a series of short fatty acid amides that possess anticonvulsant activity" PMID: 2231336 [PubMed—indexed for MEDLINE].

Abdulla Haj-Yehia, et al. "Structure-Pharmacokinetic Relationship in a Series of Valpromide Derivatives with Antiepileptic Activity"; Pharmaceutical Research; vol. 6, No. 8, (1989) pp. 683-689; Plenum Publishing Corporation.

Heinz Nau, et al. "Pharmacologic Evaluation of Various Metabolites and Analogs of Valproic Acid: Teratogenic Potencies in Mice"; Fundamental And Applied Toxicology; 6, 669-676 (1986).

P.E. Keane, et al. "Effect of Valproate on Brain Gaba: Comparison with Various Medium Chain Fatty Acids"; Pharmacological Research Communications; vol. 17, No. 6 (1985) pp. 547-555.

Meir Bailer, et al. "Can We Develop Improved Derivatives of Valproc Acid?"; Pharmacy World Science (1994) 16(1) 2-6.

Nina Isoherranen, et al. "Anticonvulsant Profile and Teratogenicity of N-methylcyclopropyl Carboxamide: A New Antiepileptic Drug"; Epilesia; vol. 43, No. 2, pp. 115-126 (2002); Blackwell Publishing, Inc.

Micha Levi, et al. "Pharmacokinetics and Antiepileptic Activity of Valproyl Hydroxamic Acid Derivatives"; Pharmaceutical Research; vol. 14, No. 2 (1997); pp. 213-217.

Meir Bialer, et al. "Pharmacokinetic Analysis of Tetra-Methylcyclopropane Analogues of Valpromide"I Pharmaceutical Research; vol. 13, No. 2 (1996); pp. 284-289.

P. E. Keane et al., "Effect of Valproate on brain GABA: Comparison With Various Medium Chain Fatty Acids.", Pharmacological Research Communications, Italian Pharmacological Society, vol. 17, No. 6, Jun. 1, 1985, pp. 547-555, XP-002049841.

Georges Taillandier et al., "Recherches dans la série dipropylacétique XII. Acides et alcools aliphatiques ramiflés anticonvulsivants.", European Journal of Medicinal Chemistry Chimica Therapeutica, FR, Editions Scientifique Elsevier, Paris, vol. 10, No. 5, Sep. 1, 1975, pp. 453-462, XP-002049847.

N. Fursah et al., "Valepotriates Of Some Valerianaceae Batsch Species and Preparing Formulations on the Basis Thereof," *Pharmacia*, vol. 41, No. 5, pp. 69-74, 1992.

V. Dunaev et al., "Biological Activity Of the Sum Of Valeipotriates Isolated From Valeriana Alliariifolia Adams," *Pharmacology and Toxicolgy*, No. 6, pp. 33-37, 1987.

USDA A.R.S. Dr. Duke's Phyto Chemical and Ethnobotani Cal Databases Chemicals and Their Biological Activities in: Valerian Officinalis—Common Valerian, Oct. 20, 1999.

F. Fonnum, Biochemistry, Anatomy and Pharmacology of GABA Neurons, in Psychopharmacology the Third Generation of Progress, Raven Press, 1987, pp. 173-195.

J. M. Cedarbaum et al. "Drugs for Parkin's Disease, Spasticity and Acute Muscle Spasms", in Goodman And Gilman's The Pharm. Basis of Thera., pp. 463-484, 1990.

J. W. Lance, Symposium synopsis in Spasticity—Disordered motor control, Feldman et al. (Eds), 1980, pp. 485-494.

R. Bernasconi et al., in Anticonvulsants in Affective Disorders, pp. 14-32, (Excerpta Medica 1984).

K. L. Casey, "Pain and Central Nervous System Disease: A Summary and Overview", in Pain and Central Nervous System Disease: The Central Pain Syndromes, Raven Press, 1991, pp. 1-11.

A. Danek et al., "Restless Legs Syndrome", Chapter 70, in Neurological Disorders: Course and Treatment, 1996, pp. 819-823.

P. D. Lyden, "GABA and Neuroprotection", Chapter 10, in Neuroportective Agents and Cerebral Ischaemia, IRN 40, 1997, pp. 233-258.

W. A. Hauser, "Risk Factors for Epilepsy, Chapter 1", in The Epilepsies Etiologies and Prevention, 1999 pp. 1-11.

V. E. Tyler et al., Pharmacognosy, 9th ed. (Lea and Febiger 1988), pp. 456-494.

H. A. Hare et al., The National Standard Dispensatory, 1905, pp. 93, 94, 159, 160, 169, 256, 642, 692-694, 766, 767, 1031, 1383, 1384, 1426, 1479, 1480, 1571, 1572, 1619-1620, 1631-1633, 1661-1662.

D. Hoffman, The Herbal Handbook: A User's Guide to Medical Herbalism, pp. 38, 39, 83 and 84, 1989, (Healing Arts Press).

Millspaugh, American Medicinal Plants, an illustrated and descriptive guide to the American Plants used as Homeopathic Remedies, pp. 622-626 (Dover 1974).

Duke, "CRC Handbook of Medicinal Herbs", CRC Press, 1985, p. 557.

D. Albe-Fessard et al., "Comparison of Different Animal Models of Chronic Pain" in 13 Advances in Pain Research, Mechanisms and Structure, 4th Ed., 1992, pp. 11-27.

M. Grieve, A Modern Herbal, pp. 35-40, 265-276, 381, 382, 411-415, 744-746, 781, 782, 824-830, Hafner, 1959.

R. G. Fariello et al., "Valproic Acid—Mechanisms of Action" in Antiepileptic Drugs (4th Ed.), pp. 581-588, Raven Press, 1995.

T. Nogrady, Medicinal Chemistry: A Biochemical Approach (2nd Ed.) pp. 225-239 (Oxford University Press) 1988.

J. J. Cereghino et al., "Introduction" in Antiepileptic Drugs, 4th Ed., pp. 1-11, (Raven Press), 1995.

R. H. Levy et al., "General Principles—Drug Absorption, Distribution, and Elimination", in Antiepileptic Drugs, 4th Ed., pp. 13-30, Raven Press, 1995.

H. S. White et al., "Experimental Selection, Quantification, and Evaluation of Antiepileptic Drugs", in Anti-Epileptic Drugs, 4th Ed., pp. 99-110, Raven Press, 1995.

A. S. Waters, "Circaedian Rhythm of the Restless Legs", Session No. 30, Sleep Disorders, Restless Legs Syndrome, Neurology Supp. 1995, p. A285.

J. C. Ballenger et al., "Kindling as a Model for Alcohol Withdrawl Syndromes", Brit. J. Psychiat. vol. 133, pp. 1-14, 1978.

L. J. Bertman et al., "Comparison of the antinociceptive and antispastic action . . . spinal rats", Brain Res. 684, pp. 8-18, 1995.

D. Blumer et al., Indications for Carbamazepine in Mental Illness: Atypical Psychiatric Disorder or Temporal Lobe Syndrome?, Compre. Psych., vol. 29:2, 1988, pp. 108-122.

U. Bojic et al., "Further Branching of Valproate-Related Carboxylic Acids Reduces . . . Effect"., Chem. Res. Toxicol., vol. 9, 1996, pp. 866-870.

C. K. Chai, "Influence of Aminooxyacetic Acid . . . Defect in the Mouse", Proc. Soc. Exptl. Biol. Med. vol. 109, pp. 491-495, 1962.

B. Costall et al., "Stereotyped Behavior Patterns and Hyperactivity Induced by Amphetamine and . . . Mesolimbic Nucei", Brain Research, vol. 123, pp. 89-111, 1977.

S. L. Dewey et al., "A Pharmacologic Strategy for the Treatment of Nicotine Addition", Synapse vol. 31, pp. 76-86, 1999.

M. A. Dichter et al., "New Antiepileptic Drugs", Drug Therapy, vol. 334:24, pp. 1583-1590, 1996.

N. W. Dunham et al., "A Note on a Simple Apparatus for Detecting Neurological Deficit in Rats and Mice", J. Am. Pharm. Assn. vol. 46:3, pp. 208-209, 1957.

H. M. Emrich et al., "The Use of Sodium Valproate, Carbamazepine and Oxcarbazepine in Patients with Affective Disorders", J. Affective Disorders, vol. 8, pp. 243-250, 1985.

D. A. Evans et al., "The Asymmetric Synthesis of α-Hydrazino Acid Derivatives . . . Esters", Tetrahedron, vol. 44:17, pp. 5525-5540, 1988.

A. Fadel, "Optically Active Cyclopropanols by Samarium (II) Iodide Induced Intramolecular Reductive Cyclisa-tion . . . Amides." Tetrahedron, vol. 5:4, pp. 531-534, 1994.

M. D. Ginsberg et al., Rodent Models of Cerebral Ischemia, Stroke, vol. 20:12, pp. 1627-1642, 1989.

G. V. Goddard et al., "A Permanent Change in Brain Function Resulting from Daily Electrical Stimulation", Exp. Neurology, vol. 25, pp. 295-330, 1969.

J. Halikas et al., Lancet 18:623-624, 1989.

J. Hao et al., "Depression of the flexor reflex by systemic morphine increases in chronically spinalized rats", Euro. J. Pharmacology, vol. 191, pp. 407-416, 1990.

R. Hauck et al., "The Enantiomers of Vallproic Acid . . . Highly Stereoselective Teratogenicity in Mice", Pharm. Research, vol. 9:7, 1992, pp. 850-855.

R. Hering et al., "Sodium valproate in the prophylactic treatment of migraine: a double-blind study versus Placebo", Cephalalgia, vol. 12, pp. 81-84, 1992.

R. Hering et al., "Sodium valproate in the treatment of cluster headache: an open clinical trial", Cephalalgia. vol. 9, pp. 195-198, 1989.

A. J. Hunter et al., "Animal modesl of acute ischaemic stroke: can they predict clinically successful neuropro-tective drugs?", Trends. Pharmacol. Sci., vol. 16, pp. 123-128, 1996.

S. Irwin, "Comprehensive Observational Assessment . . . Physiological State of the Mouse", Psychopharm. vol. 13, pp. 222-257, 1968.

J. Jolkkonen et al., "Seisure-induced damage to the hippocampus is prevented by modulation of the GABAergic system", Neuroreport vol. 7, pp. 2031-2035, 1996.

P. E. Keane et al., "The effects of Analogues of Valproic Acid on Seizures induced by Pentylenetetrazol and GABA Content in Brain of Mice", Neuropharm. vol. 22:7, pp. 875-879, 1983.

P. E. Keane et al., "Effect of Valproate on Brain GABA: Comparison with Various Medium Chain Fatty Acids", Pharma. Res. Comm. vol. 17:6, pp. 547-555, 1985.

W. S. Lee et al., "Peripheral GABA receptor-mediated . . . and trigeminal stimulation", British J. Pharm. vol. 116, pp. 1661-1667, 1995.

L. Lin et al., "Valerian-Derived Sedative Agents . . . Selective INEPT Nuclear Magnetic Resonance Technique", Pharm. Res. vol. 8:9, pp. 1094-1102.

W. Loscher et al., "Pharmacological Evaluation of Various Metabolites and Analogues of Valproic Acid", Neuropharm. vol. 24:5, pp. 427-435, 1985.

N. T. Mathew et al., "Valproate in the Treatment of Persistent Chronic Daily Headache. An Open Label Study", Headache, vol. 31, pp. 71-74, 1991.

T. Matsuyama et al., "Hilar Somatostatin Neurons are More Vulnerable to an Ischemic Insult Than CA1 Pyramidal Neurons", J. Cerebral Blood Flow and Metab., vol. 13, pp. 229-234, 1993.

Nau et al., "Valproic Acid Teratogenesis", Atlas Sci. Pharm. vol. 69. Pp. 52-56, 1987.

H. Nau, "Valproic Acid Teratogenicity in Mice after Various Administration and Phenobarbital Pretreatment . . . Implicated as Teratogen", Fund. And Appl. Toxic., vol. 6, pp. 662-668, 1986.

H. Nau et al., "Weak acids may act as teratogens by accumulating in the basic milieu of the early Mammalian embryo", Nature, vol. 323, pp. 276-278, 1986.

H. Nau et al., "Pharmacologic Evaluation of Various Metabolites and Analogs of Valproic Acid: Teratogenic Potencies in Mice", Fund and Applied Toxicology, vol. 6, pp. 669-676, 1986.

S. T. O'Keeffe, "Restless Legs Syndrome", Arch. Intern. Med, vol. 156, pp. 243-248, 1996.

W. L. Olson et al., "Gabapentin for Parkinsonism: A Double-Blind, Placebo-controlled, Crossover Trial", Am. J. Med., vol. 102, pp. 60-66, 1997.

R. M. Post et al., "Progressive Effects of Cocaine on Behavior and Central Amine Metabolism in Rhesus Monkeys . . . Psychosis", Biol. Psychiatry, vol. 11:4, pp. 403-419, 1976.

R. M. Post et al., "Sensitization, Kindling, and Anticonvulsants in Mania", J. Clin. Psychiatry, vol. 50:12, (Supp), 1989, pp. 23-29.

R. M Post et al., "Cocaine-Induced Behavioral Sensitization and Kindling . . . Seizures", Annals New York Academy of Sciences, vol. 537, pp. 292-308, 1988.

R. M. Post et al., "Electroconvulsive Seizures Inhibit Amygdala Kindling" . . . Affective Illness, Epilepsia, vol. 25:2, pp. 234-239, 1984.

R. M. Post et al., "The Effect of Amygdala Kindling on Spontaneous and Cocaine-Induced Motor Activity and Lidocaine Seizures", Psychopharm. vol. 72., pp. 189-196, 1981.

R. J. Racine, "Modification of Seizure Activity by Electrical Stimulation: II, Motor Seizure", Electroenceph. And Clinical Neurophy., vol. 32, pp. 281-294, 1972.

P. Sachdev et al., "Restlessness: the anatomy of a neuropsychiatric symptom" Austral. New Zealand J. Psychiatry, vol. 30: pp. 38-53, 1996.

K. Sato et al., "An analysis of anticonvulsant actions of GABA agonists (progabide and baclofen) in the kindling model of epilepsy", Epilepsy Res., vol. 5, pp. 117-124, 1990.

J. M. Silver et al., "Antiepileptogenic Effects of Conventional Anticonvulsants in the Kindling Model of Epilepsy", Ann. Neurol vol. 29, pp. 356-363, 1991.

R. S. Sloviter, "Decreased Hippocampal Inhibition and Selective Loss of Interneurons in Experimental Epilepsy", Science, vol. 235, pp. 73-76, 1987.

R. Stevens, "The Chemistry of HOP Constituents", Chem. Rev. vol. 67, pp. 19-71, 1967.

M. Swerdlow, "Anticonvulsant Drugs and Chronic Pain", J. Clinical . Neuropharmacology, vol. 7:1, 1984, pp. 51-82.

W. Tang et al., "Fluorinated Analogues as Mechanistic Probes in Valproic Acid Hepatotoxicity: Hepatic . . . Glutathione Status", Chem. Res. Toxicol. vol. 8, pp. 671-682, 1995.

C. Tober et al., "D-23129: A potent anticonvulsant in the amygdala kindling model of comples partial seisures", Eur. J. Pharmacol. vol. 15, pp. 163-169, 1996.

J. A. Wada et al., "Persistent Seizure Susceptibility and Recurrent Spontaneous Seizures in Kindled Cats", Epilepsia, vol. 15, pp. 465-478, 1974.

J. Wright et al., "The Spastic Mouse", Clin. Orthop. vol. 253, pp. 12-19, 1990.

H. Nau et al., "Valproic Acid-Induced Neural Tube Defects in Mouse . . . Pharmacokinetic and Possible Mechanisms", Pharm. & Toxicology, vol. 69, pp. 310-321, 1991.

International Search Report.

Abdulla Haj-Yehia et al., "Pharmacokinetic Analysis of the Structural Requirements for Forming "Stable" Analogues of Valpromide", Pharmaceutical Research, vol. 9, No. 8, 1992, pp. 1058-1063.

Mitsuyo Tanaka et al., "Quantitative Structure-Activity Relationships of Anticonvulsant Aralkyl and Alkyl Carbamates", Chem. Pharm. Bull. 33(6), pp. 2403-2410, 1985.

Abdulla Haj-Yehia et al., "Pharmacokinetics of a Valpromide Isomer, Valnoctamide, in Dogs", Journal of Pharmaceutical Sciences, vol. 77, No. 10, Oct. 1988, pp. 831-834.

P.E. Keane et al., "Effect of Valproate on Brain GABA: Comparison with Various Medium Chain Fatty Acids", Pharmacological Research Communications, vol. 17, No. 6, 1985, pp. 547-555.

* cited by examiner

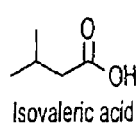
Isovaleric acid

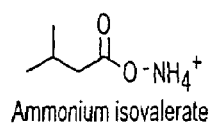
Ammonium isovalerate

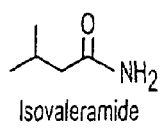
Isovaleramide

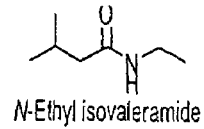
N-Ethyl isovaleramide

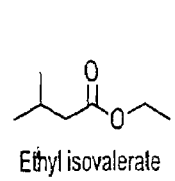
Ethyl isovalerate

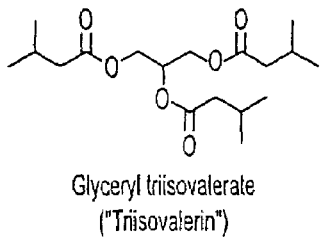
Glyceryl triisovalerate ("Triisovalerin")

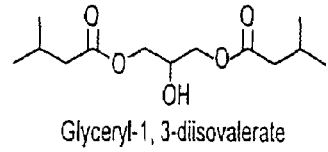
Glyceryl-1, 3-diisovalerate

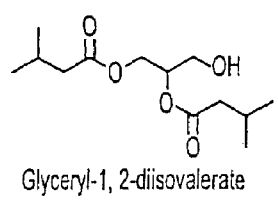
Glyceryl-1, 2-diisovalerate

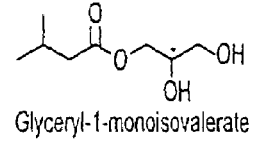
Glyceryl-1-monoisovalerate

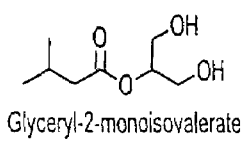
Glyceryl-2-monoisovalerate

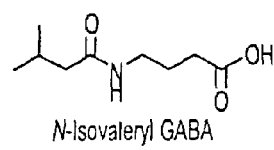
N-Isovaleryl GABA

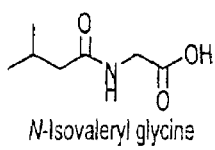
N-Isovaleryl glycine

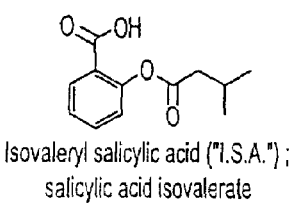
Isovaleryl salicylic acid ("I.S.A."); salicylic acid isovalerate

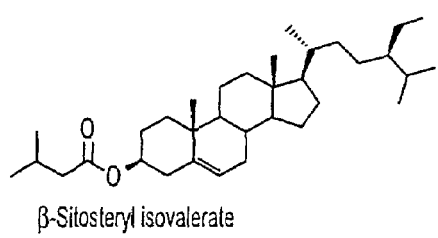
β-Sitosteryl isovalerate

Isovaleryl salicylamide (salicylamide isovalerate ester)

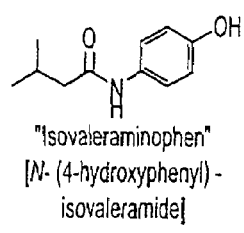
"Isovaleraminophen" [N-(4-hydroxyphenyl)-isovaleramide]

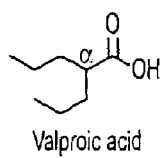
Valproic acid

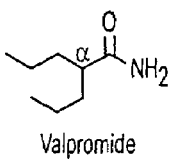
Valpromide

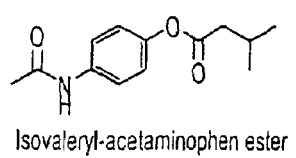
Isovaleryl-acetaminophen ester

The Structures of Isovaleramide and Related Compounds

FIG. 1a

Structures of compounds structurally related to isovaleramide

Isovaleramide and Baclofen Significantly Reduce the Flexor Reflex in a Dose-Dependent Manner in Chronic Spinalized Rats Effect of Isovaleramide on Seizure Score and Afterdischarge Duration in Amygdala-Kindled Rats Daily Administration (500mg/kg p.o.) NPS 1776 Delays the Development of Kindling Compared to Controls in a Model of Seizure Acquisition in the Amygdala-Kindled Rat

TREATING A VARIETY OF PATHOLOGICAL CONDITIONS, INCLUDING SPASTICITY AND CONVULSIONS, BY EFFECTING A MODULATION OF CNS ACTIVITY WITH ISOVALERAMIDE, ISOVALERIC ACID, OR A RELATED COMPOUND

CROSS-REFERENCE TO RELATED APPLICATIONS

This application is a divisional application of application Ser. No. 09/258,882 filed on Mar. 1, 1999, now U.S. Pat. 6,589,994 issued Jul. 8, 2003, which is a continuation-in-part application of PCT application PCT/US97/15272 filed on Aug. 29, 1997, which is a continuation of provisional application Ser. No. 60/025,050, filed Aug. 30, 1996.

The present invention provides methods of treating pathological conditions, such as spasticity and convulsions, the symptoms of which are alleviated by a modulation of activity in the central nervous system (CNS), without producing undesirable excessive sedation or muscle weakness in animal subjects, including humans. More particularly, the invention relates to the therapeutic use of isovaleramide, isovaleric acid, and related compounds in patients suffering from pathologies of this nature.

A number of pathological states, diseases, and disorders are characterized by a profound aberration in the normal function of the central nervous system (CNS). Such conditions include spasticity, strokes, spinal cord injuries, chronic neurodegenerative disorders and diseases such as Parkinson's and Huntington's diseases, Alzheimer's disease, and epilepsy. At the clinical level, these states usually only respond to pharmacologic intervention with compounds or substances that possess significant activity at the level of the CNS.

Many agents currently employed in the treatment of pathologies, such as spasticity and convulsions, display troubling side-effect profiles that limit their long-term clinical utility. Among these agents, for example, are the benzodiazepines, which can cause impairment of cognition (impairment of memory-related performance, or "cognitive blunting"). See, for example, ANTIEPILEPTIC DRUGS, Fourth Edition (Levy et al., eds.), Raven Press (1995). Two other clinically used agents are valproate and related therapeutically useful salts such as valproic acid hemisodium salt, which are hepatotoxic and teratogenic, and baclofen, which produces excessive muscle weakness and sedation. These side effects severely limit the therapeutic potential for both drugs. It is apparent, therefore, that improved and better-tolerated treatments for spasticity, convulsions, and other therapeutic indications are greatly desired.

SUMMARY OF THE INVENTION

Accordingly, it is an object of the present invention to provide a therapeutic approach for the treatment of various pathologies by effecting a modulation of CNS activity without producing excessive sedation, muscle weakness, fatigue, teratogenicity or hepatotoxicity.

It also is an object of the present invention to provide a method for alleviating one or more symptoms associated with a condition, such as spasticity, that is ameliorated by means of a centrally mediated decrease in muscle tone.

It is another object of the present invention to provide a novel anticonvulsant therapy.

It is another object of the present invention to provide a novel prophylactic therapy for migraine and other headache pathologies.

It is another object of the present invention to provide a novel therapy for affective mood disorders such as bipolar disorder.

It is another object of the present invention to provide a novel neuroprotective therapy.

It is another object of the present invention to provide a novel therapy to assist with substance withdrawal therapy and the substance cravings that often accompany such abuse.

In accomplishing these and other objectives, there has been provided, according to one aspect of the present invention, a method of using a compound selected from the group consisting of isovaleramide, a pharmaceutically acceptable ester of isovaleric acid, a pharmaceutically acceptable amide of isovaleric acid, and a compound selected from the group consisting of 2-methyl isovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido)isovaleramide, 2-methyl-1-propyl sulfonamide, 1-methylethyl sulfamate, 2-methyl-1-propyl sulfamate, isopropyl carbamate, and isobutylcarbamate.

Thus, the present invention also provides a method of treatment comprising the step of administering, to a patient suffering from a pathology that is ameliorated by a modulation of CNS activity, a therapeutically effective amount of a pharmaceutical formulation comprising a pharmaceutically acceptable carrier and a composition selected from the aforementioned group of agents.

According to one embodiment of the invention, the pharmaceutically acceptable amide of isovaleric acid is selected from the group consisting of isovaleramide, N-ethyl isovaleramide, N-methyl isovaleramide, N,N-dimethyl isovaleramide, N-methyl,N-ethyl isovaleramide, N-(2-acetamido)isovaleramide ("N-isovaleryl glycinamide"), and N-isovaleryl GABA.

According to yet another embodiment of the invention, the treated pathology is an affective mood disorder, convulsions, a central neuropathic pain syndrome, a headache, or a restlessness syndrome. In still another embodiment, the pathology is spasticity that is ameliorated by a centrally mediated decrease in muscle tone. In a further embodiment, the treated pathology is a cerebral insult, neurodegeneration, or the acquisition of epilepsy. For still another embodiment, the treated pathology is substance abuse, craving of substance, addiction, and withdrawal.

In accordance with another aspect of the present invention, a method of use is provided for an extract of Valerianaceae, cramp bark, black haw, or hops in a method of treating a symptom of spasticity, where the extract comprises at least one compound that is hydrolyzed in vivo to yield isovaleric acid or isovaleramide. By the same token, the present invention provides a method for alleviating a symptom of spasticity in a subject in need of such treatment, comprising the step of administering a therapeutically effective amount of an extract as described above.

Other objects, features, and advantages of the present invention will become apparent from the following detailed description. It should be understood, however, that the detailed description and the specific examples, while indicating preferred embodiments of the present invention, are given by way of illustration only, since various changes and modifications within the spirit and scope of the invention will become apparent to those skilled in the art from this detailed description.

BRIEF DESCRIPTION OF THE DRAWINGS

FIGS. 1a and 1b depict the structures of compounds, including isovaleramide, capable of inducing a modulation of the central nervous system.

DETAILED DESCRIPTION OF THE PREFERRED EMBODIMENTS

1. Overview

Figure 1B:
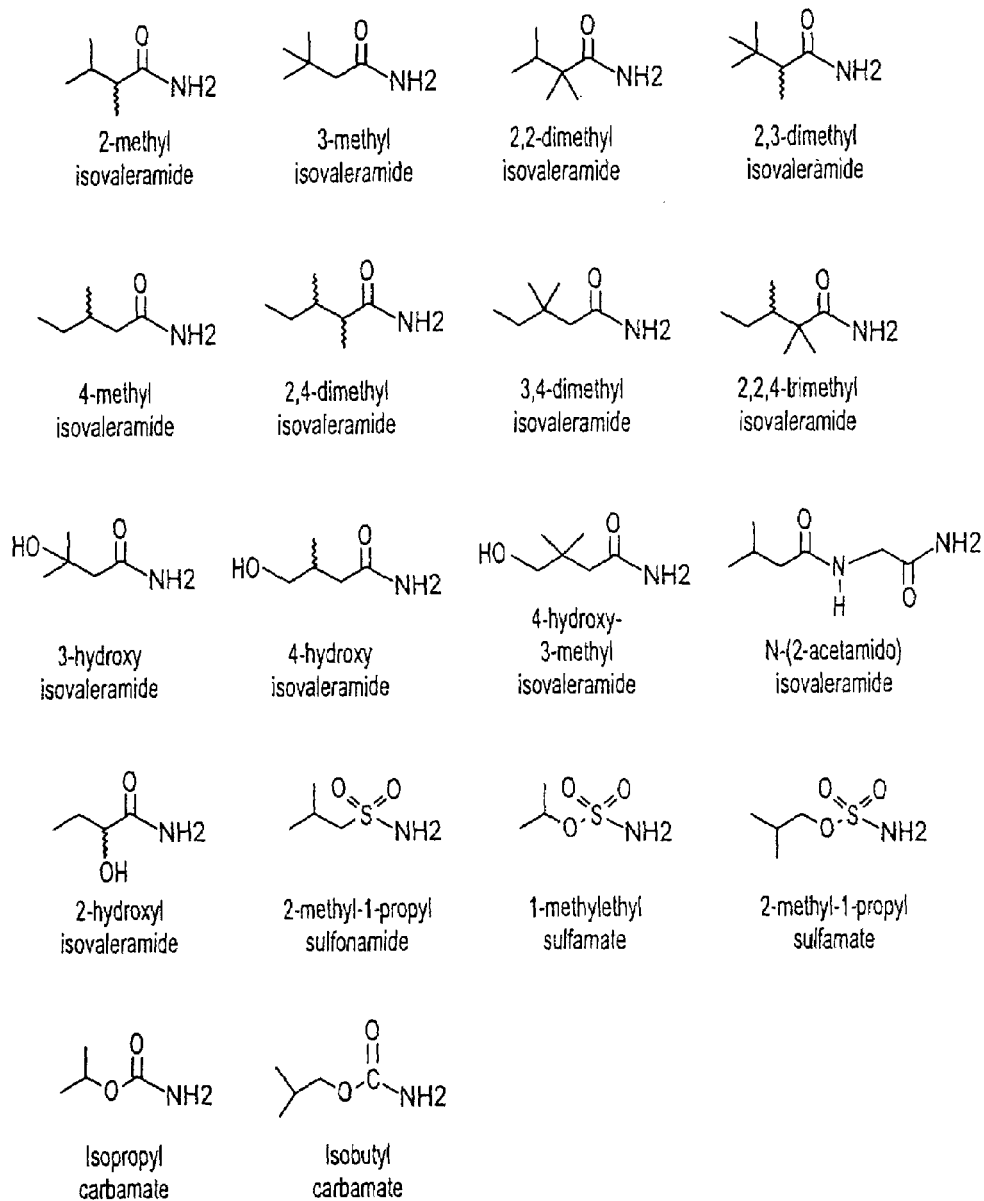

Isovaleric acid and its pharmaceutically acceptable salts, amides such as isovaleramide, and alcohol esters such as ethyl isovalerate and glyceryl triisovalerate can be administered in vivo to effect a modulation of CNS activity. A series of structurally related compounds also display similar properties. These agents modulate CNS activity by enhancing inhibitory (or decreasing excitatory) neurotransmission centrally, without complete suppression of all activity. Pursuant to the present invention, therefore, a subject receiving such an agent is not overtly sedated, anesthetized, or paralyzed in the context, for example, of decreasing seizures (while causing little or no anesthesia), decreasing muscle tone (while causing little or no accompanying paralysis), eliciting a calmative effect (with little or no sedation), or ameliorating an ambulatory syndrome such as spasticity (with little or no accompanying weakness or flaccidity).

A number of pathologies, exemplified by affective mood disorders (i.e., bipolar disorder), headaches (chronic, cluster, migraine), restlessness syndromes, neuropathic pain, movement disorders, spasticity, convulsions, cerebral insult, neurodegeneration, and substance abuse have at least one symptom that is usefully alleviated by effecting a modulation of CNS activity. Accordingly, an individual who suffers from such a pathology may be treated with a therapy where, pursuant to the present invention, that individual receives a pharmaceutical formulation of isovaleramide, isovaleric acid, or a related compound.

Without wishing to be bound by any theory, the inventors believe that the compounds of the present invention act via a GABAergic mechanism and, hence, bear a pharmacological similarity to known drugs that are considered to enhance central GABAergic neurotransmission. Like many of the extant drugs, such as the barbiturates, the benzodiazepines, gabapentin, valproic acid and therapeutically useful valproate salts, such as valproate hemisodium salt (herein included with reference to valproate), vigabatrin, and progabide, the compounds of the present invention are effective in treating pathological conditions, illustrated by those mentioned above, that are thought to arise from a defect in the regulation of inhibitory (GABA- and/or glycine-related) neurotransmission.

This regulation may occur by a direct or modulatory effect at CNS receptors or by impact on a metabolic pathway which heightens GABA or glycine levels and/or which reduces levels of an excitatory neurotransmitter like glutamate. See Ruggero et al., in ANTIEPILEPTIC DRUGS (4th ed.), pages 581-88 (Raven Press 1995); Nogrady, MEDICINAL CHEMISTRY: A BIOCHEMICAL APPROACH (2d ed.), pages 225-39 (Oxford University Press 1988); Fonnum and Morselli, respectively, in PSYCHOPHARMACOLOGY: THE THIRD GENERATION OF PROGRESS, pages 173-82 and 183-95 (Raven Press 1987).

Despite an anticipated similarity in mechanism of action, the compounds of the present invention do not engender the disadvantageous side effects associated with conventional drug therapies in this area, such as the hepatotoxicity or teratogenicity that arises with valproate administration.

2. Exemplary Pathologies Ameliorated by a Modulation of CNS Activity

SPASTICITY: Spasticity may be "defined as an upper [i.e., CNS] motor neuron disorder characterized by a velocity-dependent increase in tonic stretch reflexes (muscle tone) with exaggerated tendon jerks resulting from hyperexcitability of the stretch reflex." Lance, Symposia synopsis in SPASTICITY—DISORDERED MOTOR CONTROL, Feldman et al. (eds.) (1980) (Symposia Specialists, distributed by Year Book Medical Publishers). An increase in tonic stretch reflexes, however, is only one of the many symptoms present in a disordered motor function caused by an upper neuron lesion in a variety of neurological disorders; thus, such a disordered motor function is variable in its etiology and presentation.

Major disease states and conditions associated with spasticity include multiple sclerosis, cerebral palsy, stroke, trauma or injury to the spinal cord, and closed head trauma. There are "positive symptoms" that can occur with spasticity, such as the Babinski response, painful flexor or extensor spasms, increased or exaggerated deep tendon reflexes, and clonus. Other symptoms, referred to as "negative symptoms," include weakness, fatigue, lack of dexterity, and paralysis. It is the combination of these positive and negative signs and symptoms that is denoted clinically as "spastic paresis" (spastic paralysis). Pain, impairment of sleep, and various degrees of loss of general motor function are also associated with spasticity.

The pathological states observed in spasticity are fundamentally different at the physiological level from the commonly experienced acute muscular aches, strains, and sprains that occur from a localized external insult to a particular muscle, i.e., outside of, or peripheral to, the CNS. These pathological states also are different from the relatively common involuntary spasms of smooth muscle, such as vascular spasms, bladder spasms, and bronchial spasms. Such non-spastic (non-CNS), peripheral or localized symptoms are commonly treated with so-called "antispasmodic" or "spasmolytic" agents. Such agents generally are not useful in treating spasticity. Cedarbaum & Schleifer, "Drugs for Parkinson's Disease, Spasticity and Acute Muscle Spasms," in GOODMAN AND GILMAN'S THE PHARMACOLOGICAL BASIS OF THERAPEUTICS, 8th ed. [hereafter GOODMAN AND GILMAN'S], pages 463-484 (Pergamon Press 1990).

The pharmaceutical formulations employed in accordance with the present invention can effect a centrally mediated decrease in muscle tone and, hence, are useful for the acute or chronic alleviation of one or more symptoms of spasticity. In the context of the present invention, "spasticity" refers to a heightened tone of skeletal muscle which is manifested by symptoms exemplified by but not limited to painful flexor or extensor spasms, increased or exaggerated deep tendon reflexes, hyperreflexia, loss of dexterity, muscular weakness, exaggerated tendon jerks, and clonus. The phrase "antispasticity agent" refers here to a composition that is useful for the symptomatic treatment of spasticity, as demonstrated by the alleviation of at least one of the following manifestations of spasticity: painful flexor or extensor spasms, increased or exaggerated deep tendon reflexes, hyperreflexia, loss of dexterity, muscular weakness, exaggerated tendon jerks, and clonus. Accordingly, the "alleviation" of spasticity refers here to the lessening of one or more symptoms of spasticity, including, but not limited to, painful flexor or extensor spasms, increased or exaggerated deep tendon reflexes, hyperreflexia, loss of dexterity, muscle weakness, exaggerated tendon jerks, and clonus.

Spasticity is associated with multiple sclerosis, stroke, head trauma, spinal cord injuries, cerebral palsy, and other neurodegenerative diseases, disorders, and conditions. Spasticity is distinct from acute muscle spasms, which may be associated with a variety of conditions different from those leading to spasticity. These acute muscle spasm-causing conditions include trauma, inflammation, anxiety, and/or pain.

The difference between spasticity and acute muscle spasms is illustrated by the fact that agents useful for the treatment of muscle spasms are not useful for treating spasticity associated with chronic neurological diseases. Cedarbaum & Schleifer (1990), supra. Likewise, agents used heretofore to treat spasticity associated with chronic neurological disorders have not been employed in treating acute muscle spasms, except for the benzodiazepines, such as diazepam (Valium®), which are recognized also to have muscle-relaxant activity as well as anxiolytic and anticonvulsant properties. By contrast, the present invention achieves a centrally mediated decrease in muscle tone which, in turn, addresses the particular symptoms of spasticity.

CONVULSIVE DISORDERS: Due to the widespread availability of reasonably predictive and experimentally accessible animal models of convulsant states, a number of clinically useful anticonvulsants have been prepared and developed. For example, see Cereghino et al., "Introduction," in ANTIEPILEPTIC DRUGS, 4th ed., pages 1-11 (Raven Press 1995). In many patients, seizures can be controlled with currently available antiepileptic drugs, but 25 to 30 percent of patients continue to have seizures despite optimal therapy, while many others experience unacceptable side effects. Dichter et al., *Drug Therapy* 334: 1583 (1996).

Thus, many anticonvulsants in clinical use are plagued by the occurrence of significant side effects, including troublesome daytime sedation, cognitive impairment, muscular weakness, tolerance, gingival hyperplasia, blood dyscrasias, teratogenicity, and potentially fatal hepatotoxicity. Many of these side effects are especially of concern in the clinical management (treatment) of epilepsy in children.

The present invention can be used to treat convulsive disorders such as epilepsy. That is, the pharmaceutical compositions of the invention display "anticonvulsant activity," which is evidenced by a reduction of the severity, number, and/or duration of convulsions in animal models of epilepsy. Accordingly, the inventive pharmaceutical compositions should be useful in treating conditions including, but not limited to, simple partial seizures, complex partial seizures, generalized tonic-clonic seizures, secondarily generalized seizures, status epilepticus, and trauma-induced seizures, as occur following head injury or surgery.

Epilepsy is a common disorder with many causes, and can be very difficult to treat, often requiring treatment for many years to keep seizures under control. No satisfactory treatment for epilepsy currently exists in a substantial proportion of patients. Different patients often have a better response to one drug than another, even when the patients have similar types of seizures and the drugs have similar mechanisms of action. The frequency and severity of side effects also varies substantially. Dichter et al. (1996), supra.

The pharmaceutical compositions of the invention display "anticonvulsant activity," evidenced by a reduction of the severity, number, and/or duration of convulsions in animal, models of epilepsy. Accordingly, the inventive pharmaceutical compositions should be useful in treating conditions including, but not limited to, simple partial seizures, complex partial seizures, secondarily generalized seizures, status epilepticus, and trauma-induced seizures, as occur following head injury or surgery.

AFFECTIVE MOOD DISORDERS: Included within the rubric of affective mood disorders are conditions ranging from depression to dysphoric mania, i.e., bipolar mood disorder, mania, schizoaffective disorder, traumatic brain injury-induced aggression, post-traumatic stress disorder, panic states, and behavioral dyscontrol syndromes. Affective mood disorders have been treated primarily prophylactically, with lithium salts, since the 1950s in Europe and since the 1970s in the United States. Emrich et al., *J. Affective Disorders* 8: 243-50 (1985). In recent years, alternatives to lithium treatment have been under development, given the several problems with lithium therapy. Newer, alternative therapies to lithium for affective mood disorders are anticonvulsants such as carbamazepine, benzodiazepines, valpromide, and valproate. Bernasconi et al., in ANTICONVULSANTS IN AFFECTIVE DISORDERS, pages 14-32 (Excerpta Medica 1984). Valproate has a lower propensity towards depressed arousal and mentation, memory impairment, and cognitive blunting than is seen with the benzodiazepines.

Despite the demonstrated efficacy of valproate in a multitude of affective disorders, the hepatotoxicity, teratogenicity, and gastric upset observed with its administration highlights the need for new therapeutic agents and treatments with improved side effect profiles. A pharmaceutical formulation according to the present invention is effective to this end, especially with respect to improved side effects. It is anticipated that isovaleramide and related compounds will demonstrate an absence of the type of side effects that significantly detract from the clinical usefulness of valproate. Thus, several studies of various analogs and metabolites of valproic acid have led to defined structural requirements for teratogenesis (Nau and Hendrickx, *Atlas Sci. Pharmacol. Toxicol.* 69: 310-321, (1987); Bojic, et al., *Chem. Res. Toxicol.* 9:866-870, (1996); Nau et al., *Pharmacology and Toxicology* 69: 310-321, (1991); Nau, *Fundamental and Applied Toxicology* 6: 662-668, (1986); Nau and Scott, *Nature* 323: 276-278, (1986).; Hauck and Nau, *Pharmaceutical Research* 9: 850-855, (1992); and Nau and Loscher, *Fundamental and Applied Toxicology* 6: 669-676, (1986) and hepatoxicity (Tang et al., *Chem. Res. Toxicol.* 8: 671-682, (1995)). Valproic acid itself is teratogenic (Nau and Hendrickx, 1987). Some of the structural elements required for teratogenic activity in vivo are: a free carboxyl group (stable amides exhibit significantly lower teratogenicity, or to be non-teratogenic); substituents on C-2 larger than a methyl group, and a double or triple bond at C-4. Addition of a methyl group at C-3 to valproic acid reduces teratogenicity.

NEUROPATHIC PAIN SYNDROMES: Conditions in this category, involving "neuropathic pain," affect a significant number of patients suffering from disorders of the brain or spinal cord, such as stroke, trauma, multiple sclerosis, and diabetes. Casey, in PAIN AND CENTRAL NERVOUS SYSTEM DISEASE (Raven 1991). Several known anticonvulsant compounds are efficacious in various analgesia models relevant to identifying therapeutic candidates for treating neuropathic pain. See Lloyd & Morselli, in PSYCHOPHARMACOLOGY: THE THIRD GENERATION OF PROGRESS (Raven Press 1987). In a related vein, the use of anticonvulsants like valproate to treat various pain states has been documented extensively. Swendlow, *J. Clin. Neuropharmacol.* 7: 51-82 (1984). Thus, a pharmaceutical formulation of the present invention will be applied in similar fashion to ameliorate neuropathic pain.

HEADACHES: Headaches of the migraine type (Hering & Kuritzky, *Cephalalgia* 12: 81-84 (1992)), the cluster type (Hering & Kuritzky, loc. cit. 9: 195-98 (1989)) and the chronic type (Mathew & Sabiha, *Headache* 31: 71-74 (1991)) have been treated by the administration of valproate and other anticonvulsants. The compositions of the present invention also will alleviate symptoms associated with each of the three headache types, without the adverse side effects of valproate and other anticonvulsant therapy.

RESTLESSNESS SYNDROME: The phrase "restlessness syndrome" denotes a somatic (non-mental) restlessness characterized by involuntary movement of the limbs, as well as by a sense of physical (rather than mental) agitation, which is independent of mood and, hence, is distinguished from restlessness per se. See Sachdev et al., *Austral. New Zealand J. Psychiatry* 30: 38-53 (1996).

The genus of restlessness syndromes, inclusive of numerous indications, can be observed in association with many organic and non-organic psychiatric illnesses. For example, drug-induced restlessness (tardive, chronic, and withdrawal akathisias), such as drug-induced extrapyramidal symptoms, is one of the most common side effects of neuroleptic drug therapy. Also within the restlessness-syndrome rubric are the so-called "restless leg syndrome" and "sleep-related periodic leg movements," pathologies that can be associated with head and/or spinal cord trauma and with lesions of the spinal cord. Idiopathic restless leg syndrome follows an autosomal dominant inheritance, with a variable clinical expression of symptoms.

Diminished GABAergic neurotransmission is implicated in the neurochemical basis of restlessness syndromes. Consistent with this notion, for instance, is the efficacy of the benzodiazepines, baclofen, valproate, and gabapentin in the treatment of restless leg syndrome, an important indication. See O'Keefe, *Arch. Intern. Med.* 156: 243-48 (1996); Danek et al., in NEUROLOGICAL DISORDERS: COURSE AND TREATMENT, pages 819-23 (Academic Press 1996); Mellick & Mellick, *Neurology* 45(suppl): 285-86 (1995). More generally, the present invention provides an effective therapy for restlessness syndromes with minimal side effects.

MOVEMENT DISORDERS: Various agents with known effects on the GABAergic system have been shown to decrease the dyskinetic movement characterizing movement disorders such as Parkinson's disease, Huntington's chorea, tardive dyskinesia, and stiff-man syndrome. This fact has highlighted a role for central GABAergic function in the control and modulation of CNS excitability and movement. Lloyd & Morselli (1987), supra. A method of treatment according to the present invention that can effect an altered level of CNS activity, presumably via a GABAergic mechanism, will alleviate one or more symptoms of a movement disorder.

NEUROPROTECTION: Excitatory neurotransmitters such as glutamate and aspartate, as well as a variety of voltage-gated ion channels, are thought to play a central role in mediating cell death after a variety of cerebral insults including, but not limited to, ischemia, trauma, seizure and hypoglycemia. Many studies have shown that compounds or therapeutic strategies that decrease excitatory neurotransmission, for example, glutamate antagonists, ion channel blockers, and the like, elicit a neuroprotective effect in animal models of cerebral insults.

Recent studies have shown that compounds such as GABAergic agents (chlormethiazole, valproate or muscimol) that enhance inhibitory neurotransmission, also can elicit a neuroprotective effect following the same type of cerebral insults described above (Lyden, Chapter 10 in "Neuroprotective Agents and Cerebral Ischaemia," IRN 40, Academic Press Limited, 1997). GABA and glycine are the primary inhibitory neurotransmitters in the mammalian central nervous system and, therefore, it is expected that enhancement of inhibitory neurotransmission via GABA or glycine agonists, as well as via other agents that have been shown to increase GABA or glycine inhibitory neurotransmission (GABA/glycine reuptake inhibitors, GABA/glycine metabolic inhibitors, GABA/glycine synthesis enhancers, GABA/glycine receptor modulators, etc.), also will produce a neuroprotective effect. Studies have shown that the combination of the GABA agonist muscimol and the glutamate antagonist MK-801 appeared to confer an added neuroprotective effect over either agent alone, although the effect was modest (Lyden, 1997).

Kindling has been proposed as a model to search for drugs with antiepileptogenic efficacy (Wada, *Epilepsia* 19: 217-227, (1974); Sato et al., *Epilepsy Research* 5: 117-124, (1990)); Silver et al., *Ann. Neurol.* 29: 356-363, (1991)). The term "antiepileptogenic" refers to the idea of inhibiting the processes that underlie the development of epilepsy. "Anticonvulsant", on the other hand, refers to the actual inhibition of seizures in an epileptic model.

Various anticonvulsants that have been shown to delay the acquisition of seizures in animal models of kindling have been proposed to be antiepileptic versus anticonvulsant i.e., the compounds are neuroptotective and block the development of seizures rather than merely blocking the seizure once the disorder is in place (Antiepileptic Drugs, Fourth Edition, Chapter 7., White, H. S. et al., Chapter 7, Experimental Selection, Quantification, and Evaluation of Antiepileptic Drugs (99-110) in *Antiepileptic Drugs, Fourth Edition* edited by R. H. Levy, R. H. Matson, and B. S. Meldrum, Raven Press Ltd., (1995)). Seizure kindling models are characterized by giving a sub-seizure eliciting electrical or chemical stimulus (i.e., sub-threshold) over a period of time (Goddard et al., *Exp. Neurol.* 25: 295-330, (1969)). The majority of initially non-convulsive animals that are exposed to such stimuli over a number of days, eventually exhibit seizure activity to these stimuli, have a permanently lowered threshold, exhibit altered manifestations of normal behavior and, therefore, are considered "kindled." The kindling phenomenon has been proposed to underlie the development of disorders such as certain types of epilepsy syndromes. Several kindling models of seizure development have been characterized.

Compounds that have been shown to delay or block acquisitions of seizures in these kindling models have been suggested to be a possible effective therapy following cerebral insults including, but not limited to, ischemia, haemorrhagic stoke, trauma, infection, seizure and hypoglycemia that can lead to an elevated incidence of seizure disorders (The Epilepsies: Etiologies and Prevention, 1999, Eds. Kotagal and Luders).

SUBSTANCE ABUSE/CRAVING: Anticonvulsants such as cambamazepine, that have shown efficacy in kindled models of epilepsy, have also demonstrated efficacy in reducing the symptoms of affective mood disorders and substance abuse/craving in patients (Post, et al., *Ann. N.Y. Acad. Sci.* 537:292-308, (1988)); Post, et al., *Epilepsia* 25: 234-239, (1984)); Post, et al., *Psychopharmacology* 72: 189-196, (1981)) Halikas et al., 1989; Blumer et al., 1988). Post and Kopanda (1976) have demonstrated a pharmacologic (chemical) kindling model employing subconvulsive doses of cocaine as the stimulus. The progressive human response to high cocaine usage such as irritability, restlessness, hypervigilance, and paranoia may be a human equivalent of the kindling phenomenon observed in animals.

Several kindling models of seizure development have been characterized. Seizure kindling models are characterized by administration of a sub-seizure eliciting electrical or chemical stimulus (i.e., sub-threshold) over a period of time (Goddard et al.; 1969). The majority of initially non-convulsive animals that are exposed to such stimuli over a number of days eventually exhibit seizure activity to these stimuli, have a permanently lowered threshold, exhibit altered manifestations of normal behavior and, therefore, are considered "kindled." A kindling phenomenon has been proposed to underlie the development of disorders such as certain types of epilepsy syndromes, substance abuse/craving and affective mood disorders such as bipolar (Post et al. 1981, 1984, 1988, supra: Ballenger, et al., *Br. J. Psychiatry* 133: 1-14, (1978));

The pharmaceutical compositions of the invention display anticonvulsant activity and efficacy in animal models of kindling and, accordingly, the inventive pharmaceutical compositions should be useful in treating conditions associated with substance abuse/craving.

3. Methods for Preparing Pharmaceutical Formulations
Identification of Active Compounds The rhizomes and roots of *Valeriana* spp. (common name: valerian; family Valerianaceae) have been used for medicinal purposes since ancient times. The most commonly used valerian preparations include aqueous and hydroalcoholic extracts, such as tinctures, intended for oral administration. In addition, ammoniated valerian tinctures were used medicinally in the English-speaking world since at least the beginning of the seventeenth century. Hobbs, *HerbalGram* No. 21: 19-34 (1989). In the last three decades, the sedative and antispasmodic properties of valerian preparations have been attributed primarily to the presence of chemically labile monoterpenoid iridoid triester compounds called valepotriates ("valerian-epoxy-triesters(-ates)").

The most common and abundant of the valepotriates, valtrate and didrovaltrate, each contain two isovalerate moieties esterified to a "central" iridoid nucleus. Lin et al., *Pharm. Res.* 8: 1094-02 (1991). These acid- and heat-labile substances do not survive intact in the stomach following oral administration, but readily release two moles of isovaleric acid for every mole of valepotriate. Furthermore, aqueous extracts of valerian rhizomes and roots retain their biological properties, even though the valepotriate triesters are water-insoluble. Bos et al., *Phytochem. Anal.* 7: 143-51 (1996).

The major, water-soluble, active principle of commonly used valerian extracts and other preparations, such as aqueous or hydroalcoholic extracts or tinctures, has been determined to be the ester hydrolysis product, isovaleric acid. Ammonium isovalerate and isovaleramide are produced in ammoniated tinctures. Balandrin et al., *J. Toxicol.-Toxin Rev.* 14: 165 (1995). The structures of isovaleramide and related compounds are depicted in FIG. 1a and 1b. *In this way, the chemically labile valepotriates and other valerian-derived monoterpenoid-isovalerate esters, such as bornyl, lavandulyl, and ethyl isovalerates, might be considered to act as "pro-drugs" and chemical precursors for isovaleric acid, its salts, and isovaleramide.*

Isovaleramide has been isolated from valerian plants, most probably as an isolation artifact following treatment with ammonia. Buckova et al., *Psychopharm.* 26: 308 (1977); *Chem. Abstr.* 88: 86063z (1978); see also Bos et al. and Fuzzati et al., *Phytochem. Anal.* 7: 143, 76 (1996). More recently, isovaleramide was shown to exhibit low acute toxicity in vivo, no mutagenic potential, and clinically useful anxiolytic properties (U.S. Pat. No. 5,506,268; PCT application WO 94/28,888). Methods for preparing isovaleramide are well known.

Extracts of medicinal plants that are useful for treating the symptoms of spasticity can be prepared by aqueous, hydroalcoholic, or alcoholic extraction, or by extraction with other suitable solvents using methods well known to those skilled in the art. In the context of the present invention, useful extracts contain at least one of the following: isovaleric acid, its salts or complexes, ethyl isovalerate, isovaleramide, N-ethyl isovaleramide, and their chemical precursors. Useful extracts also share the common property of releasing isovaleric acid and/or isovaleramide upon hydrolysis in vivo. Standard methods for preparing such extracts can be found in pre-1950 editions of the U.S. PHARMACOPOEIA (U.S.P.) and the NATIONAL FORMULARY (N.F.), as well as in well-known references such as Gennaro (Ed.), REMINGTON'S PHARMACEUTICAL SCIENCES, 18th ed. (Mack Publishing Co. 1990), Tyler et al., PHARMACOGNOSY, 9th ed. (Lea and Febiger 1988), and Hare et al., THE NATIONAL STANDARD DISPENSATORY (Lea Brothers 1905). Additional citations appear in U.S. Pat. No. 5,506,268 and PCT application WO 94/28,888.

The principal historic sources of naturally occurring isovaleric acid have been valerian rhizomes and roots, as well as those of closely related plants in the family Valerianaceae. As discussed by Hobbs (1989), supra, these include the common valerian plant, *Valeriana officinalis* L., as well as the East Indian valerian, *V. wallichi* DC., and the biblical spikenard, *Nardostachys jatamansi* (Roxb.) DC. In addition to valerian rhizomes and roots, other plants which have been used traditionally as sedative herbal medicines are known to contain, or to produce, isovaleric acid. These include hops (*Humulus lupulus* L., family Moraceae, which is often used in herbal formulations in combination with valerian), "cramp bark" or "guelder rose" (*Viburnum opulus* L., family Caprifoliaceae), and "black haw" (*V. prunifolium* L., root bark). Hare et al., THE NATIONAL STANDARD DISPENSATORY, pages 93, 94, 159, 160, 169, 256, 642, 692-694, 766, 767, 932, 1031, 1383, 1384, 1426, 1479, 1480, 1571, 1572, 1619, 1620, 1631-1633, 1661, and 1662 (Lea Brothers 1905); Heyl et al., *J. Am. Chem. Soc.* 42: 1744 (1920); Grier, *Pharm. J. Pharm.* 68: 302 (1929); Grier, *Chem. Drug.* (*London*) 110: 420 (1929); Grieve, A MODERN HERBAL, pages 35-40, 265-276, 381, 382, 411-415, 744-746, 781, 782, and 824-830 (Hafner 1959); Holbert, *J. Am. Pharm. Assoc., Sci. Ed.* 35: 315 (1946); Hoffmann, THE HERBAL HANDBOOK: A USER'S GUIDE TO MEDICAL HERBALISM, pages 38, 39, 83 and 84 (Healing Arts Press 1989).

As in the case of valerian rhizomes and roots, hops generate isovaleric acid from more chemically complex precursors upon oxidation or enzymatic breakdown. Millspaugh, AMERICAN MEDICINAL PLANTS, AN ILLUSTRATED AND DESCRIPTIVE GUIDE TO THE AMERICAN PLANTS USED AS HOMEOPATHIC REMEDIES, pages 622-626 (Dover 1974); Hare et al., THE NATIONAL STANDARD DISPENSATORY, pages 766-767 (Lea Brothers 1905); Grier, *Chem. Drug.* (London) 110: 420 (1929); Grieve, A MODERN HERBAL, pages 411-415 (Hafner 1959); Stevens, *Chem. Rev.* 67: 19 (1967); Duke, CRC HANDBOOK OF MEDICINAL HERBS, page 557 (CRC Press 1985).

Pharmaceutically acceptable salts of organic acids, such as isovaleric acid, which have been approved by the U.S. Food and Drug Administration for commercial marketing include sodium, potassium, lithium, zinc, aluminum, calcium, and magnesium salts. REMINGTON'S PHARMACEUTICAL SCIENCES, 18th ed., page 1445 (Mack Publishing Co. 1990). Salts of isovaleric acid that are commercially available in the United States include the ammonium, sodium, potassium, and zinc isovalerates.

Pharmaceutically acceptable alcohols can form esters with isovaleric acid by methods that are well known in the art. See, for example, March, ADVANCED ORGANIC CHEMISTRY: REACTIONS, MECHANISMS, AND STRUCTURE, fourth ed. (John Wiley and Sons 1992). Such alcohols may contain more than one hydroxyl moiety, and are well tolerated in vivo. Examples of suitable alcohols include ethanol, certain carbohydrates and related compounds such as glucose, fructose, sucrose, xylose, and lactose, sugar alcohols such as dulcitol, mannitol, and sorbitol, sugar acids such as gluconic and glucuronic acids, glycerol, the polyol inositol, benzyl alcohol, certain phenols such as phenol, salicylic acid, saligenin, salicylamide, vanillin, p-hydroxycinnamic acid (p-coumaric acid), caffeic acid, ferulic acid, gallic acid, ellagic acid, quercetin, and eugenol. Other examples of suitable alcohols include alkaloids and biogenic amines such as ephedrine, pseudoephedrine, phenylpropanolamine, tyramine, and dopamine, vitamins such as ascorbic acid (vitamin C), thiamine (vitamin B1), riboflavin (vitamin B2), pyridoxine (vitamin B6), cyanocobalamin (vitamin B12), the tocopherols (vitamin E), choline, folic acid, and pantothenic acid, monoterpenoid alcohols such as geraniol, nerol, and linalool, naturally occurring triterpenoid alcohols such as α- and β-amyrins, lupeol, and oleanolic and ursolic acids, bile acids such as cholic acid, deoxycholic acid, and taurocholic acid, and common naturally occurring plant sterols (phytosterols) such as β-sitosterol, stigmasterol, campesterol, and brassicasterol. Tyler et al., PHARMACOGNOSY, 9th ed. (Lea and Febiger 1988). Other such well-tolerated hydroxyl-containing compounds can be readily identified by those skilled in the art, for example, by consulting standard reference works such as THE MERCK INDEX and REMINGTON'S PHARMACEUTICAL SCIENCES, 18th ed. (Mack Publishing Co. 1990). Esters of isovaleric acid that are commercially available in the United States include the bornyl, ethyl, n-butyl, isoamyl, and geranyl isovalerates.

Isovaleric acid, ammonium isovalerate, and the esters ethyl isovalerate, isoamyl isovalerate, 2-methylbutyl isovalerate, cinnamyl isovalerate, methyl isovalerate, bornyl isovalerate, isobornyl isovalerate, and menthyl isovalerate are approved by the FDA and are listed in the Code of Federal Regulations as being acceptable flavoring agents which may be used in foods. 21 CFR §172.515 (1991). Valerian (*Valeriana officinalis* L.) rhizomes and roots and black haw (*Viburnum prunifolium* L.) bark are listed as acceptable natural flavoring substances and natural adjuvants in 21 CFR §172.510 (1991). Hops and "lupulin" are listed among substances that are generally recognized as safe ("GRAS"). 21 CFR §182.20 (1991).

Generally, esters of isovaleric acid are expected to be hydrolyzed in vivo by ubiquitous esterase enzymes, thereby releasing isovaleric acid and the constituent alcohol. Particularly preferred among the isovalerate esters are glyceryl mono-, di-, and especially tri-isovalerates ("triisovalerin"), isovaleryl salicylic acid or salicylate (salicylic acid isovalerate), ethyl isovalerate, and β-sitosteryl isovalerate. See FIGs. 1a 1b. *Hydrolysis of these isovalerate esters in vivo releases isovaleric acid and glycerol (glycerin), salicylic acid (an analgesic, anti-inflammatory, and febrifuge), ethanol (ethyl alcohol or common "alcohol," a CNS depressant), and β-sitosterol (a harmless phytosterol), respectively. With the exception of ethyl isovalerate, these esters are non-volatile or only slightly volatile, thereby minimizing any unpleasant odors. Furthermore, in pure form, these esters possess the advantage of having neutral to pleasant odors, in contrast to the extremely unpleasant odors of isovaleric acid and its salts, such as the ammonium, sodium, potassium, and zinc isovalerate salts. Moreover, whereas ethyl isovalerate is a liquid, the glycerylmono-, di-, and tri-isovalerates, isovaleryl salicylate, and β-sitosteryl isovalerate are expected to be solids at room temperature, thereby facilitating their formulation into various standard solid and liquid oral dosage forms well known in the art, such as tablets (e.g., uncoated tablets, enteric-coated tablets, and film-coated tablets), capsules, gelcaps, powders, concentrates (drops), elixirs, tinctures, and syrups.*

In addition to isovaleramide, various N-substituted amides of isovaleric acid may be used in the inventive methods. These amides can be prepared by methods well known in the art. See, for example, March, ADVANCED ORGANIC CHEMISTRY: REACTIONS, MECHANISMS, AND STRUCTURE, 4th ed. (John Wiley and Sons 1992). Preferred amides include N-ethyl isovaleramide, N-methyl isovaleramide, N, N-dimethyl isovaleramide, N-methyl,N-ethyl isovaleramide, N-(2-acetamido)isovaleramide ("N-isovaleryl glycinamide"), and N-isovaleryl GABA. See, for example, Tanaka et al., *J. Biol. Chem.* 242: 2966 (1967).

The present invention also is directed to compounds and methods of using compounds that, by virtue of their structural similarity to isovaleramide, share similar pharmacological activities. These compounds generally share the common structure:

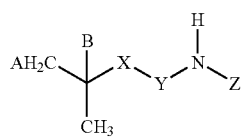

Where
A=H, CH$_3$ or OH,
B=H, OH, or CH$_3$,
X=CH$_2$, CHCH$_3$, C(CH$_3$)$_2$, —O—, CH(OH)—, or —CH$_2$O—,
Y=—CO—, or —SO$_2$—, and
Z=H, CH$_2$CO$_2$H, or CH$_2$CONH$_2$ The structures of these compounds are shown in FIGs. 1a and 1b and include substituted isovaleramides such as 2-methylisovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, and 2,2-dimethyl-n-butyramide. For each of these compounds that contains one or more asymmetric centers, the present invention specifically includes each of the possible enantiomeric or diastereomeric forms of the compound.

N,N-Diethyl isovaleramide ("Valyl"), although purported to possess CNS depressant (sedative) activity, recently has been shown to possess CNS stimulant (convulsant) properties; see U.S. Pat. No. 5,506,268 and PCT application WO 94/28,888, supra. An amide of isovaleric acid with p-aminophenol also can be prepared using standard methods to provide a compound, "isovaleraminophen," which is related structurally to the drug acetaminophen (Tylenol®; see FIG. 1a). In a manner analogous to that of the isovalerate esters, these substituted amides should be hydrolyzed in vivo (in this case, via hepatic amidase enzymes), releasing isovaleramide or isovaleric acid.

In addition to the amide compounds described above, the present invention also is directed to certain sulfonamide, sulfamate, and carbamate compounds that, by virtue of their structural similarity to isovaleramide, share similar pharmacological activities. Preferred sulfonamides and sulfamates include 2-methyl-1-propylsulfonamide, 1-methylethyl sulfamate, and 2-methyl-1-propyl sulfamate. Preferred carbamates include isobutylcarbamate (CH$_3$)$_2$CHCH$_2$OCONH$_2$) and isopropylcarbamate (CH$_3$)$_2$CHOCONH$_2$).

Certain of the compounds and preparations discussed above represent alternative forms for delivering isovaleric acid or isovaleramide in vivo. In cases such as isovaleryl salicylate and ethyl isovalerate, the pharmacologically active moiety corresponding to the alcohol portion may be expected to exert its own pharmacological effects. For example, compounds such as "isovaleraminophen" would be expected to exhibit a "Tylenol®-like" effect, similar to acetaminophen as well as the effect expected from the isovaleric acid or isovaleramide moiety. Such novel chemical combinations of a previously known, pharmacologically active alcohol, phenol, or primary or secondary amine with isovaleric acid fall within the scope of the present invention. Similar chemical combinations with 2-methylisovaleric acid, 3-methylisovaleric acid, 2,2-dimethylisovaleric acid, 2,3-dimethylisovaleric acid, 4-methylisovaleric acid, 2,4-dimethylisovaleric acid, 3,4-dimethylisovaleric acid, 2,2,4-trimethylisovaleric acid, 3-hydroxyisovaleric acid, 4-hydroxyisovaleric acid, 4-hydroxy-3-methyl-isovaleric acid, 2-hydroxyisovaleric acid, and 2,2-dimethyl-n-butyric acid are within the scope of the present invention.

Preparation of Active Compounds

The compounds of the present invention may be prepared using synthetic methods that are well known in the art. For example, many of the carboxylic acid precursors of the amide compounds are commercially available, for example, from the Aldrich Chemical Co., Milwaukee, WI, and can be converted into the corresponding amide by preparation of the acid chloride with thionyl chloride or oxalyl chloride, followed by reaction with ammonia or an amine. For compounds containing a hydroxyl group distal to the carboxyl group, the hydroxyl group first is protected using a suitable protecting group as described, for example, in Green, "Protective Groups in Organic Synthesis," Wiley (1981), prior to preparation of the acid chloride. 2-hydroxy and 3-hydroxy isovaleramide are metabolites of isovaleramide in vivo, and can be isolated in high yield from the urine of a patient being treated with isovaleramide.

For compounds where the starting acid is not commercially available, the required acid can be prepared by straightforward methods of organic synthesis known to the skilled chemist. For example, carboxylic acid esters may be deprotonated with a strong non-nucleophilic base, such as lithium diisoropylamide, followed by alkylation with methyl iodide or methyl trifluoromethanesulfonate. The alkylated ester is hydrolyzed and converted to the amide by the methods described above.

When the compounds contain one or more asymmetric centers, the individual enantiomers may be prepared from optically active starting materials, or separated by traditional methods of resolution, such as fractional crystallization of salts with chiral amines, or by preparation of amides with chiral amides, chromatographic separation, and hydrolysis of the amides. Alternatively, the amides can be prepared by well known methods of asymmetric synthesis, such as alkylation of an ester or amide of the acid prepared using a chiral auxiliary. See, for example, Evans et al, *Tetrahedron*, 44:5525 (1988) and Fadel et al. *Asymmetry* 1994:531.

Preparation of Pharmaceutical Compositions

The present invention also is directed to pharmaceutical compositions containing the active compounds described above. The pharmaceutical compositions can contain a single active compound, or can contain combinations of two or more of the active compounds. The pharmaceutical formulations of the present invention can be prepared according to known methods to prepare pharmaceutically useful compositions, whereby active agents are combined in a mixture with a pharmaceutically acceptable carrier. For instance, see REMINGTON'S PHARMACEUTICAL SCIENCES and GOODMAN AND GILMAN'S, both cited above. A composition is said to be in a "pharmaceutically acceptable carrier" if its administration can be tolerated by a recipient patient. Sterile phosphate-buffered saline is one example of a pharmaceutically acceptable carrier. Other suitable carriers (e.g., saline and Ringer's solutions) are well known to those skilled in the art. See, for example, REMINGTON'S PHARMACEUTICAL SCIENCES, supra.

In general, the dosages of the antispasticity and anticonvulsant agents described herein will vary depending upon such factors as the patient's age, weight, height, sex, general medical condition, and previous medical history. For purposes of therapy, a compound of the present invention and a pharmaceutically acceptable carrier are administered to a subject in need of such treatment in a therapeutically effective amount.

The combination of active agent and carrier is said to be administered in a "therapeutically effective amount" if the amount administered is physiologically significant. An agent is physiologically significant if its presence results in a detectable change in the physiology of a recipient patient. In the present context, for example, an antispasticity agent is physiologically significant if the presence of the agent results in the alleviation of one or more symptoms of spasticity, while an anticonvulsant agent is physiologically significant if the presence of the agent results in the reduction of the severity, number, or duration of convulsions. Similarly, for each of the pathologies recited above, a compound is physiologically significant if, upon administration to a patient, it can alleviate or reduce a clinically recognized symptom of that pathology.

Isovaleramide and related compounds can be administered orally using solid oral dosage forms such as enteric-coated tablets, caplets, gelcaps, or capsules, or via liquid oral dosage forms such as syrups or elixirs. The indicated dosage of isovaleramide and related compounds as antispasticity agents is on the order of 50-1200 mg per dose or 1-20 mg/kg body weight. Unit solid oral dosage forms preferably contain about 50-800 mg per tablet or capsule, which typically would be taken 1-2 at a time for a maximum of four times per day, at a dosage of 1-20 mg/kg body weight. Liquid formulations can also be employed with active ingredient compositions so as to provide 1-2 teaspoonfuls per dose. Furthermore, corresponding reduced dosage pediatric chewable and liquid oral dosage forms also can be administered. These compounds also can be added to foods and beverages in the form of drops (with a dropper from a "concentrate" preparation) for oral administration. In addition, compounds such as isovaleramide may be formulated into chewing gum to facilitate oral delivery and absorption.

Alternatively, isovaleramide and related compounds can be administered by injection or other systemic routes, such as IV, transdermal or transmucosal administration, for example, nasally, buccally, or rectally, via suppositories. Oral administration is much more convenient, however, and therefore is preferred. For use in an oral anticonvulsant composition, the dosage level of active ingredient(s) is on the order of 50-1200 mg per dose or 1-20 mg/kg body weight.

In addition to a use in humans, isovaleramide and related compounds can be used, for example, as antispasticity agents or anticonvulsant agents, in animals such as cats, dogs, birds, horses, cattle, mink, poultry, and fish. In such cases the active compound may be administered by injection or other systemic routes, such as transdermal or transmucosal administration (for example, rectal administration via suppositories), or orally by addition to food or drink. As an antispasticity agent, the indicated oral dosage of isovaleramide and/or related compounds per kilogram of body weight of such animals is about 50-1200 mg/kg, depending upon the species of animal and the route of administration.

The indicated oral dosage of isovaleramide and/or related compounds per kilogram body weight as anticonvulsant agents for animals is in the range of about 50-1200 mg/kg, depending upon the species of animal and the route of administration.

The present invention thus contemplates a variety of pharmaceutical compositions containing the active compounds described above (including isovaleramide, isovaleric acid, and/or its pharmaceutically acceptable salts, substituted amides, alcohol esters, sulfonamide, sulfamate, and carbamate analogs) as active ingredients that are suitable for oral, IV, parenteral, transdermal, transmucosal, intranasal, buccal, or rectal administration. Although such compounds may be present as incidental by-products in certain pharmaceutical formulations which are outside the scope of the present invention, the common feature of the present formulations is that isovaleramide, isovaleric acid, and/or its pharmaceutically acceptable salts, substituted amides, alcohol esters, and sulfonate, sulfamate, and carbamate analogs, are present in a standardized amount. That is, the pharmaceutical formulations contain a predetermined, chemically defined, and quantifiable amount of at least one of such compounds to enable the determination of the quantity of a particular composition required to achieve the dosage levels described herein.

It is further understood that isovaleramide and/or related compounds can be used in combination with other pharmaceutically active ingredients.

4. Demonstrating Therapy-Implicating Activity

The suitability and effectiveness of a given pharmaceutical formulation for the alleviation of a pathology, as discussed above, can be demonstrated using animal models such as (but not limited to) those described below.

(a) The Mutant Spastic Mouse

The mutant spastic mouse is a homozygous mouse that carries an autosomal recessive trait of genetic spasticity. The mouse is normal at birth, and then the mouse develops a coarse tremor, abnormal gait, skeletal muscle rigidity, and abnormal righting reflexes at two to three weeks of age. No structural abnormalities have been found. Rather, the mouse has a deficit of glycine receptors throughout the central nervous system. Drugs that either potentiate the binding or synthesis of GABA, such as valproate and the benzodiazepines, are effective compounds to ameliorate some of the symptoms of spasticity in this model, as well as in humans.

The assessment of spasticity in the mutant spastic mouse can be performed by electrophysiological assessment similar to the EMG recordings described below. One can also, on a more crude scale, measure righting. These mice have an abnormal delayed righting reflex when placed on their backs. Any righting reflex over one second is considered abnormal. Most normal mice cannot even be placed on their backs. Tremor can be evaluated by holding mice by their tails and rating the tremor subjectively by "absent," "slight," "moderate," or "severe." Flexibility is assessed by placing the mouse on a glass object with smoothly rounded grooves and rims. The glass object is lifted about 12 inches above the table and slowly tilted until almost vertical. Normal mice will climb about the object for a minute or more before falling to their feet. Spastic mice usually remain stiffly in one position and soon fall onto their backs. Chai et al., *Proc. Soc. Exptl. Biol. Med.* 109: 491 (1962).

(b) The Acute/Chronic Spinally Transected Rat and the Acute Decerebrate Rat

There are several models of spasticity including the acute decerebrate rat, the acute or chronic spinally transected rat, and the chronically spinal cord-lesioned rat. (Wright, J., et al., Clin Orthop 253:12, 1990). The acute models, although of proven value in elucidating the mechanisms involved in the development of spasticity, have come under criticism due to the fact that they are acute. The animals usually die or have total recovery from spasticity. The spasticity develops immediately upon intervention, unlike the spasticity that evolves in the human condition of spasticity, which most often initially manifests itself as a flaccid paralysis. Only after weeks and months does spasticity develop in humans. Some of the more chronic-lesioned or spinally transected models of spasticity do postoperatively show flaccid paralysis. At approximately four weeks post-lesion/transection, the flaccidity changes to spasticity of variable severity. Although all of these models have their own particular disadvantages and lack of true representation of the human spastic condition, they have provided much information about the nature of spasticity. These models have also provided methods to test various treatment paradigms that have led to similar treatments being tested in humans. Many of these models have also made use of different species, such as cats, dogs, and primates. Baclofen, diazepam, and tizanidine, effective antispastic agents in humans, are effective on different parameters of electrophysiologic assessment of muscle tone in these models.

(c) Primary Observation Irwin Test in the Rat

This method is based on that described by Irwin, *Psychopharmacologia* 13: 222-57 (1968). It is used to detect physiological, behavioral, and toxic effects of a test substance, and indicates a range of dosages that can be used for later experiments. Typically, rats (three per group) are administered the test substance and are then observed in comparison with a control group given vehicle. Behavioral modifications, symptoms of neurotoxicity, pupil diameter, and rectal temperature are recorded according to a standardized observation grid derived from that of Irwin. The grid contains the following items: mortality, sedation, excitation, aggressiveness, Straub tail; writhes, convulsions, tremor, exophthalmos, salivation, lacrimation, piloerection, defecation, fear, traction, reactivity to touch, loss of righting reflexes, sleep, motor incoordination, muscle tone, stereotypies, head-weaving, catalepsy, grasping, ptosis, respiration, corneal reflex, analgesia, abnormal gait, forepaw treading, loss of balance, head twitches, rectal temperature, and pupil diameter. Observations are performed at 15, 30, 60, 120, and 180 minutes following administration of the test substance, and also 24 hours later. The test substance can be administered intraperitoneally (i.p.) subcutaneously (s.c.) or orally (p.o.).

(d) Rotarod Test in the Rat and Mouse

This is a test of neurological deficits using the method described by Dunham et al., *J. Am. Pharm. Assoc.* 46: 208-09 (1957). Rats or mice are placed on a rod rotating at a speed of eight turns per minute. The number of animals which drop off the rod before three minutes is counted and the drop-off times are recorded (maximum: 180 seconds). Ten rats are studied per group and the test is performed blind. The test compound is administered i.p. 60 minutes prior to testing. Diazepam, a benzodiazepine, is administered at 8 mg/kg, i.p., as the reference substance. A control group administered the vehicle is also included in the study.

(e) Anticonvulsant Activity

There are numerous in vivo models involving different kinds of seizures and behavioral effects that are relevant for clinically distinct forms of epilepsy. It therefore is prudent to test for effects in several models, because it may be an oversimplification to suppose that the same mechanism underlies all forms of seizure activity.

One useful model is provided by the Frings audiogenic seizure-susceptible mouse, a model of reflex epilepsy. At the time of testing, individual mice are placed into a round Plexiglas chamber and exposed to a sound stimulus of 110 decibels, 11 kHz, for 20 seconds. Animals not displaying tonic hindlimb extensions were considered protected. In addition, the seizure score for each mouse can be recorded as: (1) running for less than 10 seconds; (2) running for greater than 10 seconds; (3) clonic activity of limbs and/or vibrissae; (4) forelimb extension/hindlimb flexion; and (5) hindlimb extension.

The average seizure score can be calculated for each group of mice employed in the dose-response study. At each dose, mice are also tested on a rotarod for testing of motor impairment (toxicity). Testing for motor impairment on the rotarod involves placing a mouse for a three-minute trial period on a one-inch diameter rod rotating at six revolutions per minute. If the mouse falls off of the rotating rod three times within the three-minute time period, it is considered a toxic response.

(f) Anti-Manic Activity

The amphetamine-induced hyperactivity model in rats can be used to assess the possible use of compounds in the treatment of affective mood disorders. In addition to being a test for classical and a typical antipsychotic activity, this procedure has also been proposed as a simple animal model of manic behavior. Costall et al., *Brain Res.* 123: 89-111 (1977).

Anticonvulsants, such as cambamazepine, that have shown efficacy in kindled models of epilepsy, have also demonstrated efficacy in reducing the symptoms of affective mood disorders and substance abuse/craving in patients (Post, *J. Clin. Psychiatry* 50: 45-47, (1989), Halikas, et al., *Lancet* 18: 623-624, (1989); Blumer et al., *Compr. Psychiatry* 29: 108-122, (1988)).

(g) Neurogenic Inflammation of the Meninges

Neurogenic inflammation within the meninges has been proposed as an event in the underlying pathology of migraine headaches. Lee et al., *Brit. J. Pharmacol.* 116: 1661-67 (1995). Compounds are tested for their ability to block the leakage of radiolabeled bovine serum albumin within the dura mater post trigeminal stimulation.

(h) Analgesic Properties

There are many whole-animal assays for determining analgesic properties, such as writhing, hotplate, tail flick, arthritic pain, paw pressure tests, and the Bennet or Chung models of neuropathic pain. Albe-Fessard et al., in 13 ADVANCES IN PAIN RESEARCH AND THERAPY, pages 11-27 (Raven Press 1990).

(i) Movement Disorders and Restlessness Syndromes

Animal models exist for the study of movement disorders and restlessness syndromes, for example, drug-induced akathisias, serotonin syndrome, rotation induced by unilateral nigral lesions. Lloyd & Morselli (1987), supra. Additionally, individual case reports of anecdotal efficacy of compounds in humans have been a source for support for these indications. Mellick & Mellick (1995), supra; Olson et al., *Am. J. Med.* 102: 60-66 (1997).

(j) Neuroprotection

Kindling has been proposed as a model that can be used to identify drugs with antiepileptogenic efficacy (Wada, 1974; Sato et al., 1990; Silver et al., 1991). The term "antiepileptogenic" refers to the idea of inhibiting the processes that underly the development of epilepsy thereby providing a "neuroprotective" effect. "Anticonvulsant," on the other hand, refers to the acutal inhibition of seizures in an epileptic model. Several models of kindling are useful. The amygdala-kindled rat is such a model (Tober, C., *Eur. J. Pharmacol.* 15: 163-169, (1996)). Seizure kindling models are characterized by giving a sub-seizure eliciting electrical or chemical stimulus (i.e., sub-threshold) over a period of time (Goddard et al.; 1969). The majority of initially nonconvulsive animals that are exposed to such stimuli over a number of days, eventually exhibit seizure activity to these stimuli, have a permanently lowered threshold, exhibit altered manifestations of normal behavior and therefore are considered "kindled."

Acute cerebral insults, such as status epilepticus, traumatic injury and stroke induce damage to selective neuronal populations in the hippocampus (Matsuyama, et al., *J. Cereb. Blood Flow Metab.* 13: 229-234, (1993)); Sloviter, *Science* 235: 73-76, (1987)) suggesting that substances designed to prevent the neuronal damage that occurs in a variety of human neurological diseases would be therapeutically useful. Jolkkonen, et al., *Neuroreport* 7: 2031-2035, (1996) found that augmentation of GABAergic inhibition by chronic infusion of the GABA transaminase inhibitor, vigabatrin, prevented the delayed seizure-induced damage following kainate-induced status epilepticus.

Stroke in humans is a highly variable clinical condition, dependent upon pre-existing disease in a patient, the site and severity of the stroke, the type of stroke (ischemic or hemorrhagic), and the time from onset to presentation for treatment. A number of animal models of stroke have been developed over the past several years to aid in our understanding of the pathophysiological mechanisms of neuronal injury and to allow for the evaluation of potential neuroprotective agents (Ginsberg et al., *Stroke* 20: 1627-1642, 1989; Hunter et al., *Trends. Pharmacol. Sci.* 16: 123-128, 1996). A major goal of these animal models has been to reduce the biological variability, by controlling or eliminating the variables mentioned above, to facilitate data analysis and interpretation. In doing so, however, these animal models do not perfectly mimic the human condition.

(k) Substance Abuse/Craving

Kindling phenomenon has been proposed to underlie the development of disorders such as epilepsy substance abuse/craving and affective mood disorders such as bipolar (Post et al. 1981: Post et al., 1984; Ballenger et al., 1978; Post et al., 1988). Anticonvulsants, such as cambamazepine, that have shown efficacy in kindled models of epilepsy, have also demonstrated efficacy in reducing the symptoms of affective mood disorders and substance abuse/craving in patients (Post and Weiss, 1989, Halikas et al., 1989; Blumer et al., 1988). Post et al., (*Biol. Psychiatry* 11: 403-419, (1976)) have demonstrated a pharmacologic (chemical) kindling model employing subconvulsive doses of cocaine as the stimulus. The progressive human response to high cocaine usage such as irritability, restlessness, hypervigilance, and paranoia, may be a human equivalent of the kindling phenomenon observed in animals. Recently, the anticonvulsant drug, vigabatrin, was proposed as a possible treatment for cocaine or nicotine craving (Dewey, et al., *Synapse* 31:76, (1999)).

The therapeutic effects of isovaleramide, isovaleric acid, and related compounds in various of the assays described above, combined with a general lack of toxicity, make the compounds of the present invention ideal agents for the treatment of the pathologies described above, including spasticity and convulsions/seizures. With this background, the present invention will be understood more readily by reference to the following examples, which are provided for purposes of illustration and are not intended to be limiting of the invention.

EXAMPLE 1

Use of a Valerian Preparation to Alleviate Symptoms of Spasticity Associated with Multiple Sclerosis A human female subject, age 42, suffering from one or more symptoms of multiple sclerosis, was experiencing a considerable amount of stress and was experiencing difficulty in getting to sleep and delayed onset of sleep at night. The sleep that did occur was disturbed by stressful dreams and frequent awakening as well. The subject also experienced frequent nighttime painful extensor spasms of the lower extremities that would often awaken the subject from her sleep. The following day, these painful extensor spasms resulted in a deep muscle pain (bruising sensation), with muscle/joint stiffness.

The subject decided to consume a preparation of valerian that was noted for its sleep-aid properties. The valerian product, "Baldriparan stark N," consists of tablets manufactured in Germany that contain extracts of valerian root, hops, and lemon balm. The coated, pressed tablets each contain 95 milligrams of a dried 70% (v/v) ethanol extract of valerian root, 15 milligrams of a dried 45% (m/m) methanol extract of hops, and 85 milligrams of a dried water extract of lemon balm. Surprisingly, the valerian preparation not only facilitated the onset of sleep and improved the quality of sleep for the subject, but it was also noticed that the painful extensor spasms were alleviated. The subject noted that upon awakening during the night to use the bathroom, she did not experience the painful extensor spasms upon getting out of bed nor the usual stiff-leg sensation. The subject continues to consume the same valerian product for the alleviation of these symptoms on an as-needed basis (prn or pro re nata) and continues to experience relief.

EXAMPLE 2

Use of a Valerian Preparation to Alleviate Symptoms of Spasticity Associated with Spinal Cord Injury A human male subject, age 38, suffers symptoms of spasticity (hyperreflexia, tendon jerks, and extensor spasms) that evolved from an earlier injury to the spinal cord. All of these symptoms interrupt and decrease the quality of sleep experienced by this individual. Upon taking the same German-made preparation of valerian described in Example 1, the subject noted considerable improvement in the quality of sleep as well as a significant reduction in night-time extensor spasms. This subject continues to consume the preparation on an as-needed (prn) basis for the alleviation of the symptoms described above.

EXAMPLE 3

Isovaleramide Antispasticity Tests (1) Assessment of Spasticity in Chronic Spinally Transected Rats In these studies, male albino Holtzman-derived rats (Harlan Sprague-Dawley Laboratories) weighing 270-530 grams were used as subjects. The animals were housed independently and had continuous access to food and water throughout the experiments.

All procedures were reviewed and approved by the Institutional Animal Care and Use Committee. Animals were anesthetized using a mixture of isoflurane and oxygen at a flow rate of 4 liters/minute.

The rats were then placed in a stereotaxic frame and anesthesia was maintained. An incision was made so that the paraspinal muscles could be retracted and a laminectomy performed between T6-T9. A one- to two-millimeter portion of the spinal cord was removed by evacuation and replaced with Gel foam to reduce bleeding, after which the incision was closed in layers.

Following the transection, rats were placed in a room in which the ambient temperature was raised to about 80° F. with a space heater to maintain body temperature. On the following morning post-surgery, the hindquarters of the spinalized rats were bathed and their urine expressed manually by applying pressure to their bladders. Experiments were conducted between 21 and 28 days after surgery. For the first two weeks, these rats were given 0.25 ml of the antibiotic Sulfatrim Pediatric Suspension orally to prevent bladder infection.

A commercial antibiotic cream was applied to any part of the skin that showed signs of decubitus lesions. Within approximately two weeks, all animals regained bladder control and were no longer given antibiotic treatment. Advokat, *Brain Res.* 684: 8 (1995). Assessment of spasticity was performed before and after drug treatment such that each animal served as its own control.

Initial assessment of spasticity was performed by the subjective scoring method of rating the resulting spasticity response elicited with an innocuous stimulus, i.e., a metal probe, that was pressed against the lower abdomen at four specific sites. The spastic reaction was evaluated for each of the four trials using a scale ranging from zero (no spastic response in all four trials) to four (a maximum, tonic-clonic reaction elicited in all four trials). All spasticity scores, pre- and post-treatment, were transformed to indicate the percent spasticity such that a score of 0/4=0%, 1/4=25%, etc. These raw or normalized scores were analyzed with a one-way repeated measures ANOVA.

Figure 2:
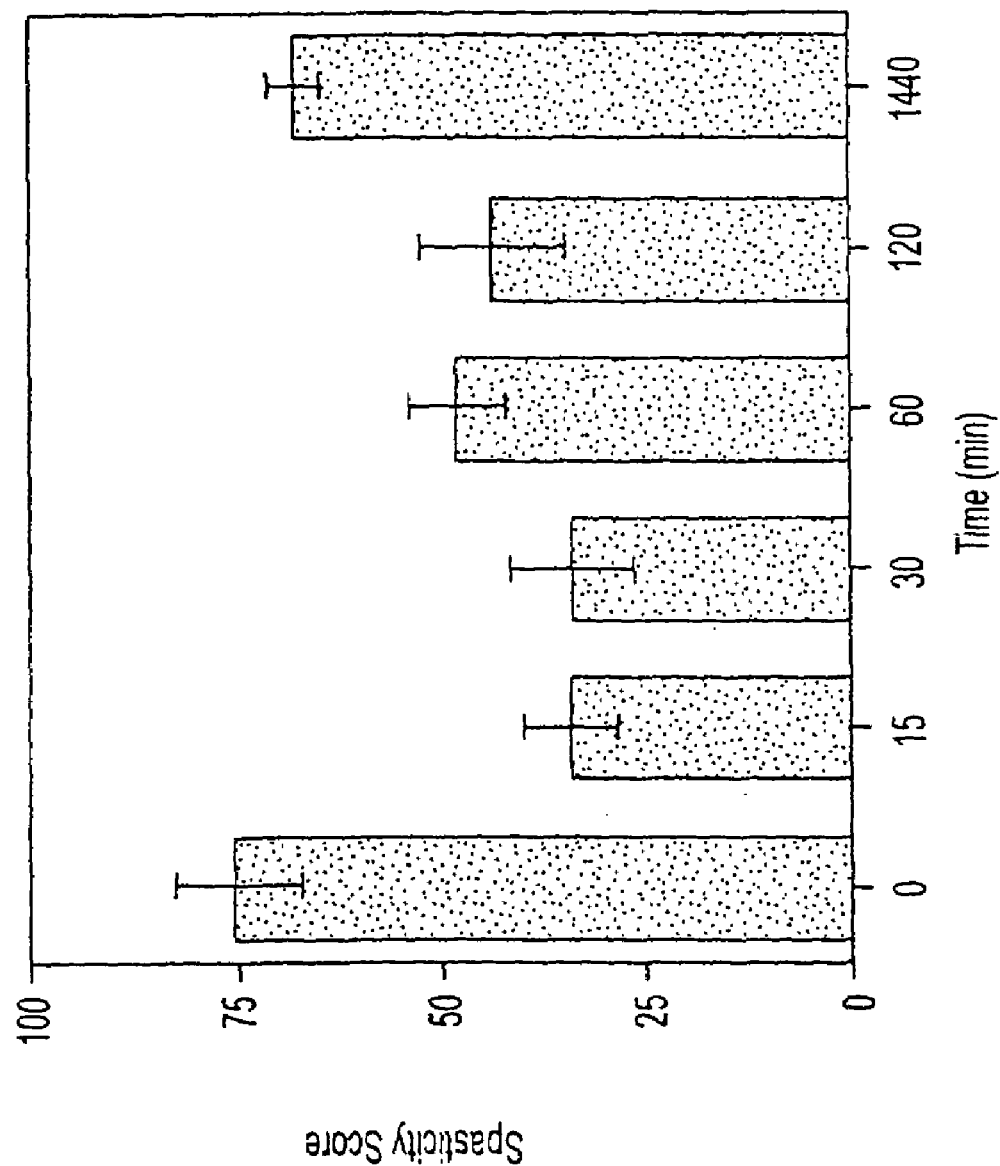
FIG. 2 portrays the effect of isovaleramide (at 300 mg/kg, i.p.) on gross observational spasticity scores elicited by a metal probe applied to the abdomen in the chronic spinalized rat. Each rat served as its own control; there were three rats per group. The bar at time zero represents pre-treatment control values.

As shown in FIG. 2, isovaleramide at a dose of 300 mg/kg, i.p., was efficacious at 15, 30, 60, and 120 minutes post-administration in reducing the spasticity scores (45-65%). By the next day, i.e., by 1440 minutes (24 hours), the spasticity scores had essentially returned to baseline values. No overt behavioral toxicity or motor impairment was observed at this dose. The rats were alert and able to grasp with their non-paralyzed front paws as were the control, untreated rats.

Figure 3:
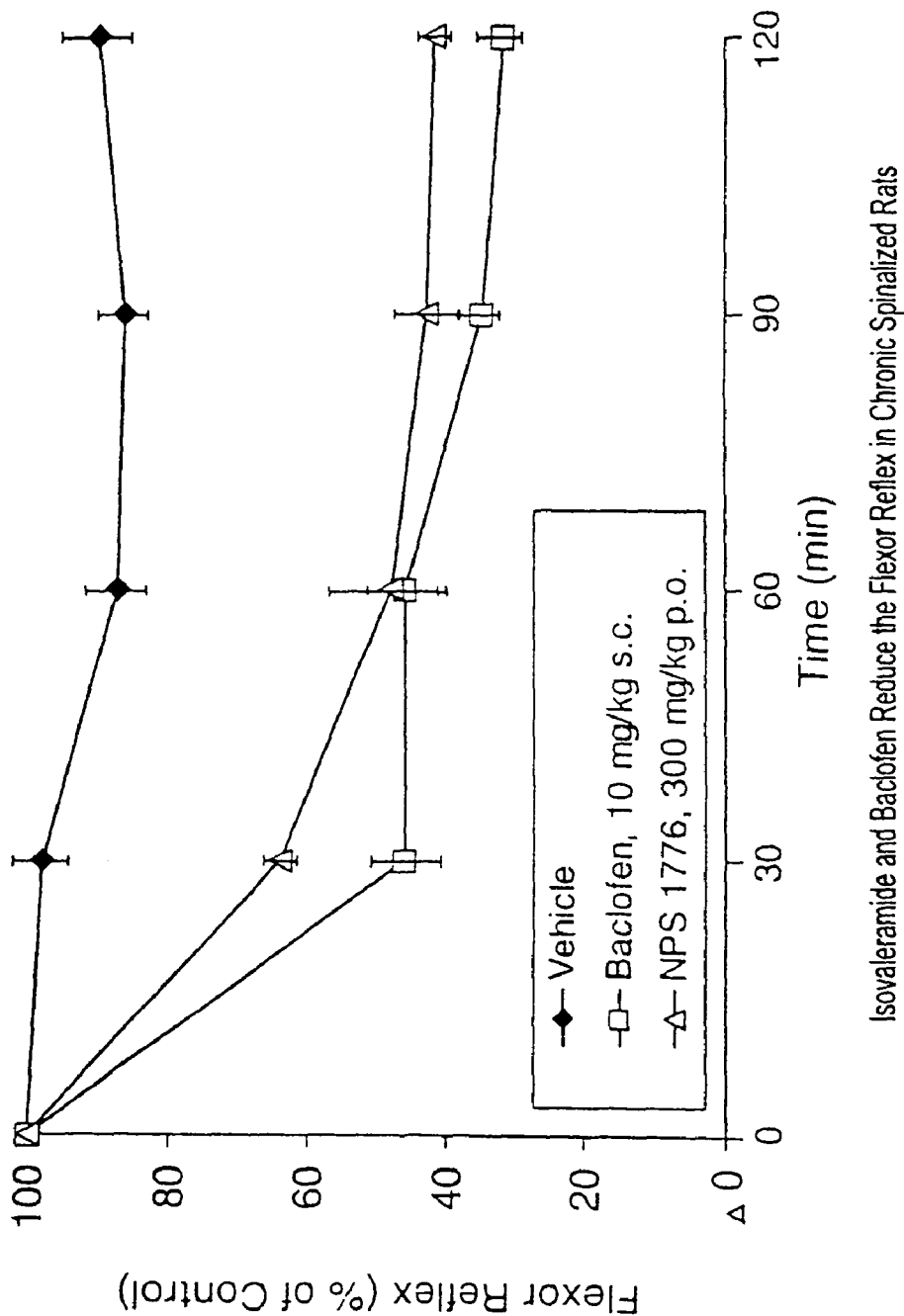
FIG. 3 illustrates a time-dependent reduction of the flexor reflex, an electrophysiological measure of spasticity, in the chronic spinalized rat. The effects of isovaleramide (300 mg/kg p.o.), baclofen (10 mg/kg s.c.), and vehicle (water, 12 ml/kg p.o.) are shown at pre-treatment (time zero) and at 30, 60, 90, and 120 minutes post-administration. Isovaleramide caused a significant decrease in the magnitude of the flexor reflex, comparable to that observed with baclofen.

With reference to FIG. 3, the polysynaptic flexor-reflex responses, to test stimuli which activate high-threshold afferents, were recorded as EMG activity from the ipsilateral hamstring muscle. Supramaximal electric shocks were applied to the hindpaw, and recording electrodes were placed in the biceps femoris semitendinosus muscle. Five sets of stimuli were made at each time point. The flexor reflex was recorded, in both the pre-drug and the post-drug periods, every 30 minutes once a stable baseline response was achieved. See Hao et al., *Eur. J. Pharmacol.* 191: 407 (1990).

Thus, the responses were determined in spinalized rats by observing the flexor-reflex response (FIG. 3) before treatment and at each of 30, 60, 90, and 120 minutes following administration of isovaleramide (300 mg/kg p.o.), baclofen (10 mg/kg s.c.) and vehicle (water, 12 ml/kg p.o.), respectively.

Isovaleramide was shown to reduce the magnitude of the flexor-reflex responses, at all time points in a chronic spinalized rat with similar efficacy to baclofen, the positive control.

Figure 4:
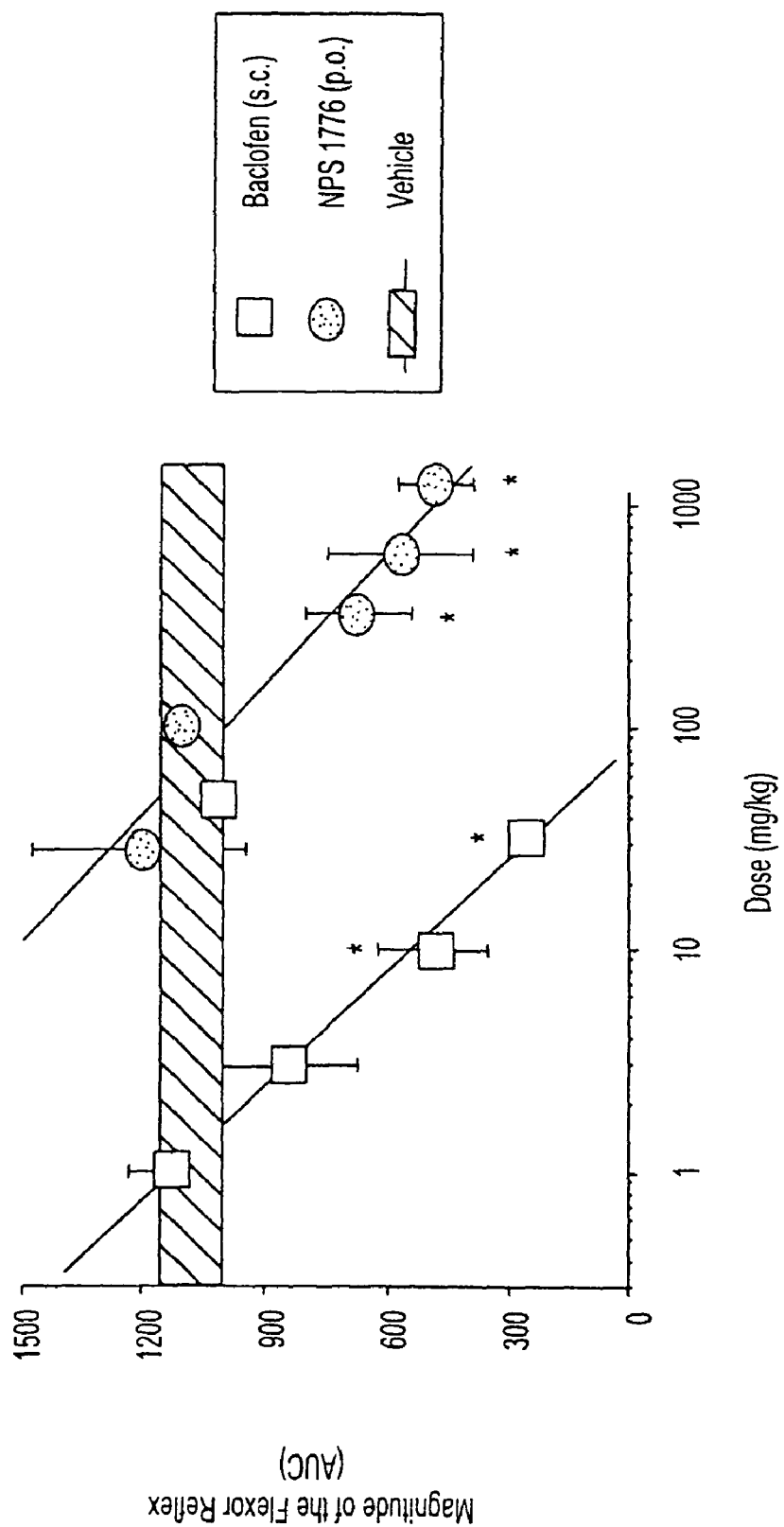
FIG. 4 shows a dose-response relationship for isovaleramide and baclofen, a known antispasticity agent. Isovaleramide and baclofen produced a similar dose-dependent reduction of the flexor reflex in the chronic spinalized rat. The responses from FIG. 3 and response from additional doses were converted to a total-area-under-the-curve for the two-hour measurement. All drug-related groups were significantly different from the vehicle ($p<0.05$, ANOVA).
Figure 5:
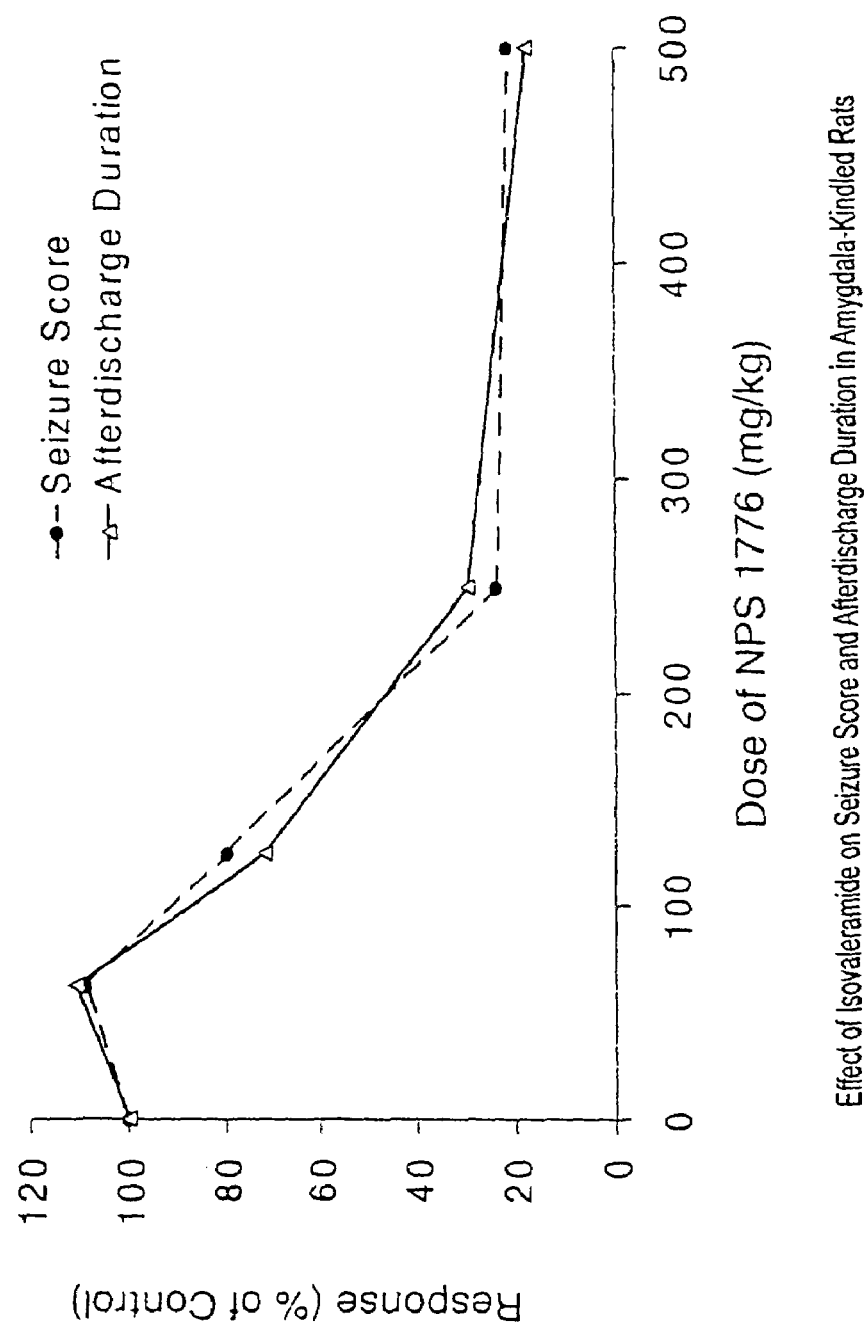
FIG. 5 shows that isovaleramide was effective in reducing, in a dose-dependent manner, the generalized seizure responses of fully kindled rats. Isovaleramide decreased the mean seizure score and the afterdischarge duration in amygdala-kindled rats, showing that it exerts anticonvulsant activity against both focal and secondarily generalized seizures.
Figure 6:
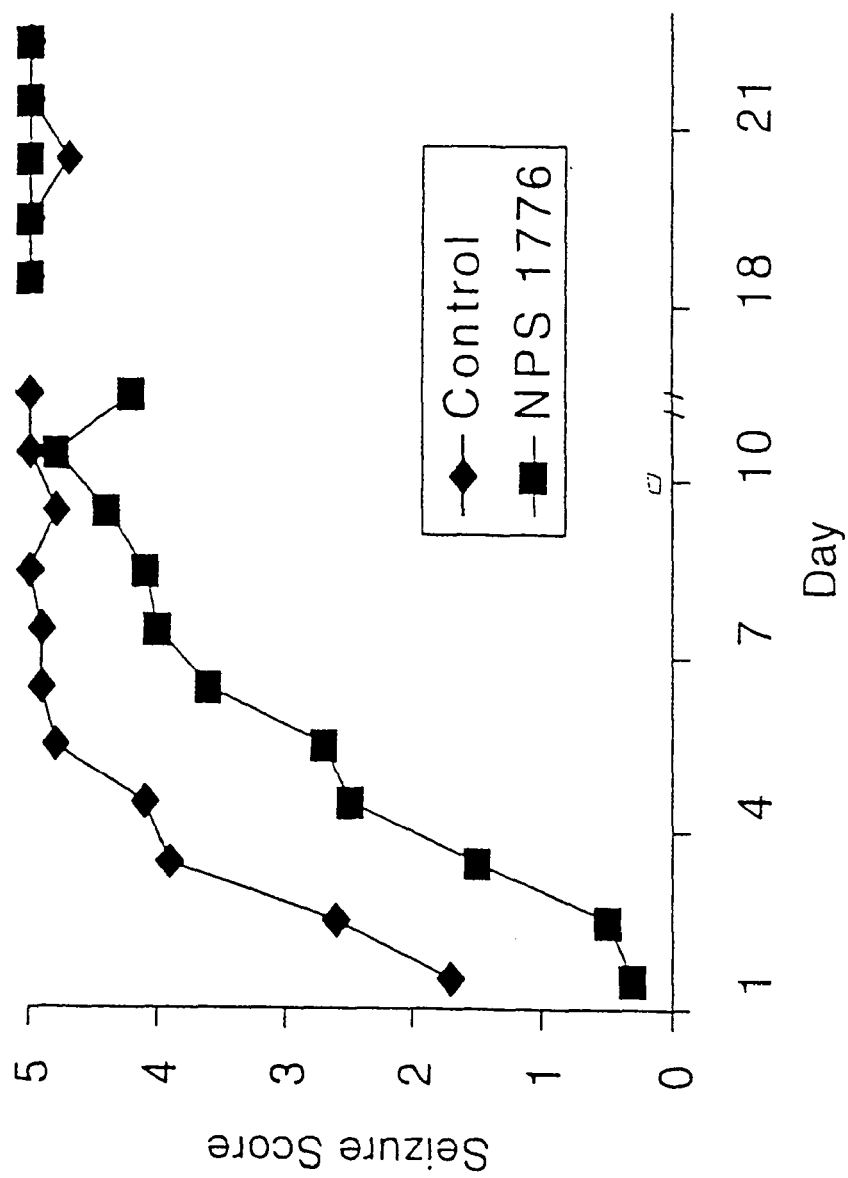
FIG. 6 illustrates the antiepileptogenesis effect of a daily 500 mg/kg p.o. dose of isovaleramide compared to controls. Isovaleramide elicited a delay in the rate of increase in both seizure score and afterdischarge duration (not shown) which normally develop during electrical kindling in the amygdala-kindled rat.

In FIG. 4, the responses from FIG. 3 and additional doses of isovaleramide and baclofen are converted to a total-area-under-the-curve format, covering the entire, two-hour measurement period. All drug-treated groups differed significantly from the vehicle (p<0.05), based on a one-way analysis of variance. Between the drug-treated groups, no differences were found in total reduction of the flexor reflex over the two-hour period (pairwise multiple comparison, Student-Newman-Keuls method).

(2) Primary Observation Irwin Test in the Rat

Administered i.p. in the rat, isovaleramide induced no changes from saline-injected controls at doses up to 256 mg/kg. At 512 mg/kg, slight sedation from 60 to 120 minutes, loss of traction (observed in only one of three rats) at 120 minutes, and decreased muscle tone from 60 to 120 minutes were observed. At 1024 mg/kg, marked sedation up to 30 minutes was observed, becoming moderate up to 120 minutes, then slight at 180 minutes. Decreased fear also was observed at this dose up to 30 minutes and in one of three rats up to 120 minutes. Decreased reactivity to touch up to 120 minutes, decreased muscle tone up to 180 minutes, slight hypothermia up to 120 minutes, and an abnormal gait (rolling) from 60 to 80 minutes were also observed at this dose. Loss of grasping and loss of righting reflex occurred, in one of three rats, at 15 minutes at this dose.

(3) Rotarod Test in the Rat and the Frings Mouse

Isovaleramide, administered at doses of 128, 256, and 512 mg/kg (i.p.) 60 minutes before a test on the rotarod, did not significantly affect rotarod performance in the rat. See Table 1. In contrast, diazepam dose-dependently decreased rotarod performance.

TABLE 1

Effects of Isovaleramide and Diazepam in the Rotarod Test in the Rat

| Dose of: | Number[b] | Drop-Off Time (sec) | | |
|---|---|---|---|---|
| Isovaleramide (mg/kg)[a] | of Rats Falling | Mean ± S.E.M. | t value | % change from control |
| 0 | 5 | 135.5 ± 18.0 | — | — |
| 128 | 6 | 134.5 ± 20.7[c] | 0.036 | −1% |
| 256 | 7 | 98.4 ± 23.3[c] | 1.261 | −27% |
| 512 | 7 | 115.9 ± 20.5[c] | 0.717 | −14% |
| Diazepam (mg/kg)[a] | | | | |
| 4 | 9 | 55.8 ± 20.6[d] | 2.909 | −59% |
| 8 | 10+ [e] | 16.3 ± 6.4[f] | 6.222 | −88% |

[a] Isovaleramide and diazepam were administered i.p. 60 minutes before the rotarod test.
[b] Ten rats per group.
[c] Not significant according to Student's t Test.
[d] p < 0.01 according to Student's t Test.
[e] p < 0.05 according to Fisher's Exact Test.
[f] p < 0.001 according to Student's t Test.

Isovaleramide, administered at doses up to 512 mg/kg (i.p.) 15 minutes before a test on the rotarod in the Frings mouse, did not affect performance significantly. In contrast, doses of 300 mg/kg, 600 mg/kg, and 1000 mg/kg (i.p.) decreased rotarod performance in 1/8, 4/8, and 8/8 of Frings mice tested, respectively.

EXAMPLE 4

Anticonvulsant Activity in the Frings Audiogenic Seizure-Susceptible Mouse Model of Epilepsy The results of Table 2 demonstrate the anticonvulsant activity of isovaleramide when administered i.p. in this animal model of epilepsy. Isovaleramide also displayed a quick onset and a relatively short duration of action. Anticonvulsant activity was noted as early as 15 minutes, but decreased substantially by two hours. All quantitative studies therefore were conducted at 15 minutes. At this time point, the median effective dose ($ED_{50}$) for protection against tonic extension was 126 mg/kg, i.p. In addition, a dose-dependent reduction in seizure score was observed at this time point. At doses markedly higher than those providing anticonvulsant activity (>300 mg/kg), animals treated with isovaleramide displayed behavioral toxicity that was characterized by their inability to maintain their balance on the rotarod. No notable toxicity was observed at doses less than 300 mg/kg. The median toxic dose ($TD_{50}$) for rotarod impairment was 531 mg/kg, i.p. Thus, the calculated protective index ($TD_{50}/ED_{50}$) was about 4.2.

Therefore, despite the relatively low potency of isovaleramide in this model, it still displayed a relatively good separation between activity and toxicity. Isovaleramide thus had a surprising and unexpected efficacy, based on existing structure-activity relationships for amides and their corresponding acids, as an anticonvulsant in the Frings audiogenic seizure-susceptible mouse model of reflex epilepsy. The activity profile of isovaleramide is similar to that of the broad-spectrum anticonvulsant, sodium valproate. Compounds similar in structure to valproate as well as isovaleric acid have been shown in previous literature to elevate GABA levels throughout the CNS. It is this function, primarily, that the anticonvulsant activity of valproate is attributed to, although other mechanisms have been suggested. Isovaleric acid, on the other hand, was reported in the literature to be inactive as an anticonvulsant, although it was reported to elicit a slight increase in GABA levels in the brains of mice. For example, see Löscher et al., *Neuropharmacology* 24: 427 (1985); Keane et al., loc. cit. 22: 875 (1983); Keane et al., *Pharmacol. Res. Commun.* 17: 547 (1985).

TABLE 2

Effect of Isovaleramide on the Audiogenic Seizure Susceptibility of Frings Mice Following Intraperitoneal Administration

| Dose of Isovaleramide (mg/kg, i.p.) | Seizure Score ± S.E.M. | Number[a] Protected of Eight Mice Tested | Number[a] Showing Toxicity of Eight Mice Tested |
|---|---|---|---|
| 75 | 4.4 ± 0.6 | 1 | 0 |
| 112.5 | 4.0 ± 0.6 | 2 | 0 |
| 150 | 2.0 ± 0.6 | 6 | 0 |
| 300 | 1.0 ± 0 | 8 | 1 |
| 600 | — | — | 4 |
| 1000 | — | — | 8 |

$ED_{50}$ for protection: 126 mg/kg (98.8 - 168[b])
$TD_{50}$: 531 mg/kg (372 - 711[b])

[a]Measured at 15 minutes.
[b]95% confidence interval.

The results of Table 3 demonstrate that isovaleramide displayed anticonvulsant activity when administered orally in this animal model of epilepsy.

TABLE 3

Effect of Isovaleramide on the Audiogenic Seizure Susceptibility of Frings Mice Following Oral Administration

| Dose of Compound (mg/kg) | Seizure Score ± S.E.M. | Number[a] Protected of Eight Mice Tested | Number[c] Showing Toxicity of Eight Mice Tested | $ED_{50}$ for protection (mg/kg) | $TD_{50}$ (mg/kg) |
|---|---|---|---|---|---|
| 100 | 4.5 ± 0.5 | 1 | — | — | |
| 200 | 2.9 ± 0.8 | 4 | — | — | |
| 300 | 1.4 ± 0.5 | 7 | 1 | 186 | |
| 600 | 0.25 ± 0.25 | 8 | 1 | (122-255)[e] | 1009 |
| 1000 | — | — | 5 | | (677-1321)[e] |
| 1500 | 0.6 ± 0.2 | 8[b] | 5 | | |
| 2000 | 0 ± 0 | 7[b,d] | 7[d] | | |

[a]Measured at 30 minutes.
[b]Tested at 4 hours
[c]Tested at 15 minutes
[d]Only seven mice tested
[e]95% confidence level The results of Table 4 and Table 5 demonstrate that the isovaleramide analogs N-(2-acetamido)isovaleramide and 2-methylisovaleramide displayed anticonvulsant activity when administered orally in this animal model of epilepsy.

TABLE 4

Effect of N-(2-acetamido) isovaleramide on the Audiogenic Seizure Susceptibility of Frings Mice Following Oral Administration

| Dose of N-(2-acetamido) Isovaleramide (mg/kg) | Number[a] Protected of Four Mice Tested at 30 minutes | Number[a] Protected of Four Mice Tested at 120 minutes | Number[a] Showing Toxicity of Four Mice Tested at 30 minutes | Number[a] Showing Toxicity of Four Mice Tested at 120 minutes |
|---|---|---|---|---|
| 30 | 0 | 0 | 0 | 0 |
| 100 | 0 | 0 | 0 | 0 |
| 300 | 0 | 0 | 0 | 0 |
| 1000 | 3 | 4 | 1 | 0 |

TABLE 5

Effect of 2-methylisovaleramide on the Audiogenic Seizure Susceptibility of Frings Mice Following Oral Administration

| Dose of 2-methyl isovaleramide (mg/kg) | Number[a] Protected of Four Mice Tested at 30 minutes | Number[a] Protected of Four Mice Tested at 120 minutes | Number[a] Showing Toxicity of Eight Mice Tested at 30 minutes | Number[a] Showing Toxicity of Eight Mice Tested at 120 minutes |
|---|---|---|---|---|
| 30 | 0 | 0 | 0 | 0 |
| 100 | 1 | 0 | 0 | 0 |
| 300 | 4 | 1 | 2[a] | 0 |

[a]no definitive signs of toxicity such as sedation or ataxia, animals just fell off In general, the historical literature on the structure-activity relationships of anticonvulsant activity around compounds similar to valproate have taught away from simple, unsubstituted compounds such as isovaleramide. It is thus a surprising and unexpected observation that isovaleramide has demonstrated an efficacy profile similar to that of valproate in the Frings audiogenic seizure-susceptible mouse model and a similar separation of activity between efficacy and toxicity as measured by rotarod performance. These observations indicate that isovaleramide is an effective therapeutic agent as a broad-spectrum anticonvulsant. Isovaleramide is known for its relative lack of toxicity in mutagenicity and cytotoxicity tests. See U.S. Pat. No. 5,506, 268 and PCT application WO 94/28,888. On the other hand, valproate has long been noted for its hepatotoxicity-causing profile. For example, see Löscher et al., *Neuropharmacology* 24: 427 (1985).

EXAMPLE 5

Anticonvulsant Activity in the Amygdala-Kindled Rat

Isovaleramide was evaluated for its ability to block the expression of amygdala-kindled seizures in fully kindled rats. Isovaleramide was evaluated for its ability to block the kindled motor seizure (seizure scores of 4 and 5) and limbic behavioral seizures (seizure score between 1-3) as well as to affect changes in afterdischarge duration.

Adult, male Sprague-Dawley rats weighing at least 230 gr were implanted with a teflon-coated bipolar electrode sterotaxically placed in the anterior basolateral nucleus of the amygdala under ketamine and xylazine anesthesia. The electrode was implanted at the following coordinates with Bregma as zero: AP-2.2 mm, ML-4.7 mm, DV-8.7 mm. After a one-week recovery period, animals were kindled to Stage 5 behavioral seizures using a stimulus consisting of a 50 Hz, 1 sec train of 1 ms biphasic 150 uA pulses that were delivered once daily until 10 consecutive stage 5 seizures were evoked. Testing of isovaleramide was initiated after a one-week, stimulus-free period. On the compound test day, rats displaying a stage 5 seizure were divided into multiple treatment groups (i.e., vehicle control and isovaleramide treatment). Sixty minutes after oral dosing, individual rats received a 300 uA, 1 sec duration stimulation and their seizure score and afterdischarge duration recorded. Seizure score was classified according to Racine (*Electroencephalogr. Clin. Neurophysiol.* 32:281-294, (1972): stage 0: no abnormal behavior; stage 1: mouth or facial movements; stage 2: mouth or facial movements and head nodding; stage 3: stage 2 and forelimb clonus; stage 4: stage 3 and rearing; stage 5: stage 4 and falling. A score of 2-3 represents a focal seizure while a score of 4-5 represents secondarily generalized seizures. Afterdischarge duration was the total duration of the amygdala electroencephalogram spikes with an amplitude of at least twice the amplitude of the prestimulus recording and a frequency greater than 1/sec.

Isovaleramide was effective in reducing in a dose-dependent manner the generalized seizure responses of fully kindled rats. Isovaleramide decreased the mean seizure score and the afterdischarge duration showing that it exerts anticonvulsant activity against both focal (seizure score 1-3) and secondarily generalized seizures (seizure score 4-5).

EXAMPLE 6

Antiepileptogenic Effect in the Amygdala-Kindled Rat

In these studies, groups of adult, male Sprague-Dawley rats weighing at least 230 gr were implanted with a teflon-coated bipolar electrode sterotaxically placed in the anterior basolateral nucleus of the amygdala under ketarine and xylazine anesthesia. The electrode was implanted at the following coordinates with Bregma as zero: AP-2.2 mm, ML-4.7 mm, DV-8.7 mm. Chronic treatment with vehicle (0.5% carboxymethylcellulose, p.o.) or isovaleramide (500 mg/kg, p.o., 0.08 ml/gr of body weight) was initiated after a seven-day postoperative recovery period. After a 30-minute pretreatment period, animals were stimulated at a suprathreshold current of 300 uA for 1 second daily (i.e, except weekends) until all control animals exhibited 7 consecutive stage 5 seizures (Racine, 1972). After 11 treatment days, all animals were permitted a 7-day drug- and stimulus-free period. Animals were then challenged with 300 uA once daily starting at day 18 until all animals displayed 5 consecutive stage 5 seizures. Seizure score and afterdischarge duration were recorded after each stimulation. Seizure score was classified according to Racine scale (1972): stage 0, no abnormal behavior; stage 1, mouth or facial movements; stage 2, mouth or facial movements and head nodding; stage 3, stage 2 and forelimb clonus; stage 4, stage 3 and rearing; stage 5, stage 4 and falling. A score of 2-3 represents a focal seizure while a score of 4-5 represents secondarily generalized seizures. Afterdischarge duration was the total duration of the amygdala electroencephalogram spikes with an amplitude of at least twice the amplitude of the prestimulus recording and a frequency greater than 1/sec. The results demonstrate the antipiletogenic effect of a daily 500 mg/kg p.o. dose of isovaleramide, which delayed the increases in both seizure score and afterdischarge duration which normally develop during electrical kindling in the amygdala-kindled rat. Although isovaleramide at this dose elicited a delay in the acquisition of seizure development, over time, the rats eventually developed full stage 5 seizures. We have shown in the Frings mouse that isovaleramide has a quick onset of action with a relatively short biological half-life. A greater antiepileptogenic effect may have occurred if the dosing schedule had been maximized for longer exposure.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the claims below.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety. The specifications of application Ser. No. 60/025,050, filed Aug. 30, 1996, and PCT application PCT/US97/15272 (published application WO 98/08498), filed Aug. 29, 1997, are specifically incorporated by reference in their entireties.

The invention claimed is:

1. A method of treating a convulsive disorder in a patient comprising administering an effective amount of isovaleramide to a patient suffering from a convulsive disorder, wherein the convulsive disorder is selected from the group consisting of simple partial seizures, complex partial seizures, generalized tonic-clonic seizures, secondarily generalized seizures, status epilepticus, and trauma-induced seizures.

2. A method of treating headaches in a patient comprising administering an effective amount of isovaleramide to a patient suffering from headaches.

* * * * *